US008329671B2

(12) United States Patent
Gu et al.

(10) Patent No.: US 8,329,671 B2
(45) Date of Patent: *Dec. 11, 2012

(54) REDUCTION OF DERMAL SCARRING

(75) Inventors: Danling Gu, San Diego, CA (US); Monica Zepeda, San Diego, CA (US)

(73) Assignee: Canji, Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/023,757

(22) Filed: Feb. 9, 2011

(65) Prior Publication Data

US 2011/0129534 A1    Jun. 2, 2011

Related U.S. Application Data

(63) Continuation of application No. 12/268,311, filed on Nov. 10, 2008, now abandoned, which is a continuation of application No. 10/997,769, filed on Nov. 23, 2004, now Pat. No. 7,465,442.

(60) Provisional application No. 60/524,993, filed on Nov. 24, 2003.

(51) Int. Cl.
  A01N 43/04    (2006.01)
  A01N 63/00    (2006.01)
  A61K 61/715   (2006.01)

(52) U.S. Cl. .......................... 514/44; 424/93.2

(58) Field of Classification Search .............. 514/44; 424/93.2
See application file for complete search history.

(56) References Cited

U.S. PATENT DOCUMENTS

| 4,394,370 | A | * | 7/1983 | Jefferies ........................ 606/76 |
| 4,975,527 | A | * | 12/1990 | Koezuka et al. ............. 530/356 |
| 5,302,706 | A | | 4/1994 | Smith |
| 5,310,728 | A | | 5/1994 | Shimizu et al. |
| 5,424,400 | A | | 6/1995 | Smith et al. |
| 5,596,079 | A | | 1/1997 | Smith et al. |
| 5,621,082 | A | | 4/1997 | Xiong et al. |
| 5,624,819 | A | | 4/1997 | Skolnick et al. |
| 5,756,283 | A | | 5/1998 | Wilson et al. |
| 5,827,702 | A | | 10/1998 | Cuthbertson |
| 5,837,511 | A | * | 11/1998 | Falck-Pedersen et al. ... 435/6.12 |
| 5,837,520 | A | | 11/1998 | Shabram et al. |
| 5,840,845 | A | | 11/1998 | Smith et al. |
| 5,851,806 | A | * | 12/1998 | Kovesdi et al. ............ 435/91.41 |
| 5,932,210 | A | | 8/1999 | Gregory et al. |
| 5,994,934 | A | | 11/1999 | Yoshimura et al. |
| 6,001,853 | A | | 12/1999 | Zigler et al. |
| 6,027,742 | A | | 2/2000 | Lee et al. |
| 6,204,251 | B1 | | 3/2001 | Cuthbertson |
| 6,210,939 | B1 | | 4/2001 | Gregory |
| 6,218,372 | B1 | | 4/2001 | Nabel et al. |
| 6,242,201 | B1 | | 6/2001 | Lane et al. |
| 6,274,614 | B1 | | 8/2001 | Richter et al. |
| 6,372,249 | B1 | | 4/2002 | Smith et al. |
| 6,475,755 | B2 | * | 11/2002 | Ciliberto et al. ............ 435/69.52 |
| 6,489,305 | B1 | | 12/2002 | Demers |
| 6,818,215 | B2 | | 11/2004 | Smith |
| 7,465,442 | B2 | * | 12/2008 | Gu et al. ..................... 424/93.2 |
| 2002/0111304 | A1 | | 8/2002 | Kazlauskas et al. |
| 2003/0175245 | A1 | * | 9/2003 | Brough et al. ............... 424/93.2 |
| 2006/0142191 | A1 | | 6/2006 | Francois et al. |

FOREIGN PATENT DOCUMENTS

| AU | B-61444 | 9/1994 |
| EP | 0640143 | 3/2001 |
| EP | 0783317 | 11/2004 |
| WO | WO 93/12251 | 6/1993 |
| WO | WO 94/09135 | 4/1994 |
| WO | WO 95/06415 | 3/1995 |
| WO | WO 95/28483 | 10/1995 |
| WO | WO 95/31995 | 11/1995 |
| WO | WO 96/12506 | 5/1996 |
| WO | WO 96/14334 | 5/1996 |
| WO | WO 96/19244 | 6/1996 |
| WO | WO 96/35704 | 11/1996 |
| WO | WO 97/03635 | 2/1997 |
| WO | WO 97/11174 | 3/1997 |
| WO | WO 97/37542 | 10/1997 |
| WO | WO 00/41647 | 7/2000 |
| WO | WO 01/13960 | * 3/2001 |

OTHER PUBLICATIONS

Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, p. 404-410).*
Pfeifer (Annu. Rev. Genomics. Hum. Genet. 2001, vol. 2, p. 177-211.*
Johnson-Saliba (Curr. Drug. Targets, 2001, vol. 2, p. 371-399).*
Shoji (Current Pharmaceutical Design, 2004, vol. 10, p. 785-796).*
Perkins (Jul. 2002, Arch. Ophthalmol. 120:941-949).*
Afshari, Cynthia A. et al.; "A Role for a p21-E2F Interaction during Senescence Arrest of Normal Human Fibroblasts"; 1996, Cell Growth & Difference, vol. 7, pp. 979-988.
Ai-Aswad, L.A. et al.; "Inhibition of fibroblast proliferation and enhancement of glaucoma filtration surgery in the rabbit with cytosine arabinoside"; 1996, Investigative Ophthalmology, vol. 37, vol. 3, p. S23, abstract.
Alcorta, David A. et al.; "Involvement of the cyclin-dependent kinase inhibitor p16 (INK4a) in replicative senescence of normal human fibroblasts."; 1996, Proc. Natl. Acad. Sci., vol. 93, pp. 13742-13747.
Ali, Robin R. et al.; "Gene transfer into the mouse retina mediated by an adeno-associated viral vector"; 1996, Hum. Mol. Genet., vol. 5, pp. 591-594.
Arteaga, Carlos L. et al; "Tissue-targeted Antisense c-fos Retroviral Vector Inhibits Established Breast Cancer Xenografts in Nude Mice"; 1996, Cancer Research, vol. 56, No. 5, pp. 1098-1103.
Atreides, Sean-Paul A. et al.; "Wound Healing Modulation in Glaucoma Filtering Surgery"; 2004, International Ophthalmology Clinics, vol. 44, No. 2, pp. 61-106.

(Continued)

*Primary Examiner* — Michael C. Wilson
(74) *Attorney, Agent, or Firm* — Kilpatrick Townsend & Stockton LLP

(57) ABSTRACT

Methods and compositions for reducing or inhibiting dermal scarring by expressing $p21^{WAF1/Cip1}$ in a wound site are provided.

8 Claims, 7 Drawing Sheets

OTHER PUBLICATIONS

Bennett, Jean et al; "Humoral Response after Administration of E1-Deleted Adenoviruses: Immune Privilege of the Subretinal Space"; 1996, Hum. Gene Ther., vol. 7, pp. 1763-1769.

Bridge, Eileen et al.; "Redundant Control of Adenovirus Late Gene Expression by Early Region 4"; 1989, Journal of Virology, vol. 63, No. 2, pp. 631-638.

Cayrol, Corinne, et al.,; "p21 binding to PCNA causes G1 and G2 cell cycle arrest in p53-deficient cells"; 1998, Oncogene, vol. 16, pp. 311-320.

Cayouette, Michel et al.; "Adenovirus-Mediated Gene Transfer of Ciliary Neurotrophic Factor Can Prevent Photoreceptor Degeneration in the Retinal Degeneration (rd) Mouse"; 1997, Hum. Gen Ther., vol. 8, pp. 423-430.

Chang, Mark W. et al.; "Adenovirus-mediated Over-expression of the Cyclin/Cyclin-dependent Kinase Inhibitor, p21 Inhibits Vascular Smooth Muscle Cell Proliferation and Neointima Formation in the Rat Carotid Artery Model of Balloon Angioplasty", 1995, J. Clin. Invest. , vol. 96, pp. 2260-2268.

Church, Invest. Ophtalmology & Visual Sci., 1981, vol. 21, No. 1, pp. 73-79.

Crystal, Ronald G.; "Transfer of Genes to Humans: Early Lessons and Obstacles to Success"; 1995, Science, vol. 270, pp. 404-410.

Dalesandro, Joy et al; "Cardiac and Pulmonary Replacement"; 1996, J. Thorac. Cardi. Surg. vol. 111, No. 2, pp. 416-422.

da Cruz L., et al., ; "Ocular gene therapy: The basic science and current state of research"; 1997, Aust N.Z. J. Opthalmol., vol. 25, pp. 97-104.

Della Neil G.; "Molecular Biology in Ophthalmology. A Review of Principles and Recent Advances.", 1996, Arch. Ophthalmol., vol. 114, pp. 457-463.

Denhardt, David T.; "Oncogene-Initiated Aberrant Signaling Engenders the Metastatic Phenotype: Synergistic Transcription Factor Interactions are Targets for Cancer Theraphy."; 1996, Crit. Rev. Oncog., vol. 7, pp. 261-291.

Deonarain, Mahendra P.; "Ligand-targeted receptor-mediated vectors for gene delivery"; 1998, Expert Opinion on Therapeutic Patents, vol. 8, No. 1, pp. 53-69.

Divan A., et al., ; "p53 expression correlates with apoptosis but not with p21, waf expression in retinoblastomas"; 1997, Journal of Pathology, vol. 182, pp. 6A.

Dunaief, Joshua L. et al.; "Retroviral Gene Transfer into Retinal Pigment Epithelial Cells Followed by Transplantation into Rat Retina"; 1995, Hum. Gene Ther. , vol. 6, pp. 1225-1229.

Eastham James A., et al.; "In vivo gene therapy with p53 or p21 Adenovirus for Prostate Cancer.", 1995, Cancer Res., vol. 55, pp. 5151-5155.

Erhardt, Joseph A. et al.; "p21.sup.WAF1 induces permanent growth arrest and enhances differentiation, but does not alter apoptosis in PC12 cells."; 1998, Oncogene , vol. 16, pp. 443-451.

Fromm, Larry et al.; "Inhibition of Cell Death by Lens-Specific Overexpression of bcl-2 in Transgenic Mice"; 1997, Dev. Genet., vol. 20, pp. 276-287.

Cartel A.L., et al.; "p21—Negative Regulator of the Cell Cycle."; 1996, Proc. Soc. Exp. Biol. Med. , vol. 213, pp. 138-149.

Gu, Danling et al; "recombinant adenovirus-p21 attenuates proliferative responses associated with excessive scarring"; 2005, Wound Rep Reg, vol. 13, pp. 480-490.

Heatly et al.; "Gene therapy using p21.sup.WAF-1/Cip-1 to modulate wound healing after glaucoma trabeculectomy surgery in a primate model of ocular hypertension"; 2004, Gene Therapy, vol. 11, pp. 949-955.

Hermens, Wim T.J.M.C. et al.,; "Transient gene transfer to neurons and glia: Analysis of adenoviral vector performance in the CNS and PNS"; 1997, J. Neurosci. Methods , vol. 71, pp. 85-98.

Johnson et al. (2001) Curr. Drug. Targets 2:371-99.

Jomary, C. et al.; "Adenovirus-mediated gene transfer to murine retinal cells in vitro and in vivo"; 1994, FEBS letters, vol. 347, pp. 117-122.

Kang, David W. et al.; "rAd-p21 to Reduce Excessive Dermal Scarring: Efficacy, Expression, and Tensile Strength in Animal Models"; 2006, Molecular Therapy, vol. 13, Supplement 1, pp. S220.

Kim, Invest. Ophtalmology & Visual Sci. 1990, vol. 31, No. 6, pp. 1183-1186.

Khaw, Peng T. et al.; "Effects of Intraoperative 5-Fluorouracil or Mitomycin C on Glaucoma Filtration Surgery in theRabbit"; 1993, Ophthalmology, vol. 100, pp. 367-372.

Koc, Omer N. et al.; "Transfer of Drug Resistance Genes Into Hematopoietic Progenitors to Improve Chemotherapy Tolerance"; 1996, Seminars in Oncology, vol. 23, No. 1, pp. 46-65.

Ledley, Fred D.; "Pharmaceutical Approach to Somatic Gene Therapy"; 1996, Pharmaceutical Research, pp. 1595-1614.

Lee, David A. et al.; "The Effects of the Fluorinated Pyrimidines FUR, FUdr, FUMP, and FdUMP, on Human Tenon's Fibroblast"; 1991, Investigation Ophthalmology & Visual Science, vol. 32, No. 9, pp. 2599-2609.

Li, Tiansen et al.; "Phenotype correction in retinal pigment epithelium in murine mucopolysaccharidosis VII by adenovirus-mediated gene transfer"; 1995, Proc. Natl. Acad. Sci. U.S.A. vol. 92, pp. 7700-7704.

Liu (Annals of plastic surgery, May 2000, vol. 44, No. 5, pp. 543-551, abstract only).

Mahmound, S. et al.; "The adenoviral E1A induces p21.sup.WAF1/CIP1 expression in cancer cells"; 2003, Biochemical and Biophysical Research Communications, vol. 305, pp. 1099-1104.

Makarov, Sergei S. et al.; "Suppression of experimental arthritis by gene transfer of interleukin 1 receptor antagonist cDNA"; 1996, Proc. Natl. Acad. Sci. U.S.A. vol. 93, pp. 402-406.

Mashhour, Babak et al.; "In vivo adenovirus-mediated gene transfer into ocular tissues"; 1994, Gene Ther. vol. 1, No. 2, pp. 122-126.

Medema, Rene H. et al., "p21.sup.waf1 can block cells at two points in the cell cycle, but does not interfere with processive DNA-replication or stress-activated kinases"; 1998, Oncogene , vol. 16, pp. 431-441.

Miller, Nicholas et al.; "Targeted vectors for gene therapy"; 1995, FASEB Journal, vol. 9, pp. 190-199.

Morgenbesser, Sharon D. et al.; "p53-dependent apoptosis produced by Rb-deficiency in the developing mouse lens."; 1994, Nature, vol. 371, pp. 72-74.

Murata, Toshinori et al.; "Ocular Gene Therapy: Experimental Studies and Clinical Possibilities"; 1997, Ophthalmic Res. vol. 29, pp. 242-251.

Nolta, Jan A. et al.; "Transduction of pluripotent human hematopoietic stem cells demostrated by clonal analysis after engraftment in immune-deficient mice"; 1996, Proc. Natl. Acad. Sci. U.S.A. vol. 93, No. 6, pp. 2414-2419.

Nussenblatt, Robert B. et al.; "Perspectives on Gene Therapy in the Treatment of Ocular Inflammation."; 1997, Eye, vol. 11, pp. 217-221.

Okamoto, Aikou et al.; "Mutations and altered expression of p16.sup. INK4 in human cancer"; 1994, Proc. Natl. Acad. Sci. U.S.A. vol. 91, No. 23, pp. 11045-11049.

Perkins, Todd W. et al.; "Adenovirus-Mediated Gene Therpy Using Human p21.sup.WAF-1/Cip-1 to prevent wound healing in a rabbit model of glaucoma filtration surgery"; 2002, Arch Ophthalmol, vol. 120, pp. 941-949.

Pfeifer et al. (2001) Annu. Rev. Genomics. Hum. Genet. 2:177-211.

Rakoczy, Piroska et al.; "Development of Gene Therapy-Based Strategies for the Treatment of Eye Diseases"; 1999, Drug Development Research, vol. 46, pp. 277-285.

Raper, Steven E. et al.; "Safety and Feasibility of Liver-Directed Ex Vivo Gene Therapy for Homozygous Familial Hypercholesterolemia"; 1996, Annals of Surgery , vol. 223, No. 2, pp. 116-126.

Sakamoto, Taiji, et al.,; "Inhibition of Experimental Proliferative Vitreoretinopathy by Retroviral Vector-mediated Transfer of Suicide Gene"; 1995, Ophthalmology , vol. 102, pp. 1417-1424.

Sakamoto, T. et al.; "A vitrectomy improves the transfection efficiency of adenoviral vector-mediated gene transfer to Muller cells"; 1998, Gene Therapy, vol. 5, pp. 1088-1097.

Scherer et al. (Sep. 2002) J. of Gene Med. 4:634-643.

Schubert Catherine A., et al.; "Retrovirus-mediated transfer of the suicide gene into retinal pigment epithelial cells in vitro"; 1997, Curr. Eye Res. , vol. 16, pp. 656-662.

Shoji et al. (2004) Current Pharmaceutical Design 10 :785-796.

Siemens et al. (2000) J. Nat. Can. Inst. 92:403-412.

Spillare Elisa A., ; "Suppresion of Growth in Vitro and Tumorigenicity in Vivo of Human Carcinoma Cell Lines by Transfected p16.sup.INK4"; 1996, Mol. Carcinog. vol. 16, pp. 53-60.

Stephan D., et al.; "Gene and other biological therapies for vascular diseases."; 1997, Fundam Clin. Pharmacol. , vol. 11, pp. 97-110.

Tsao et al.; "Adenovirus-Mediated p21 .sup.(WAF1/SDII/CIP1) Gene Transfer Induces Apoptosis of Human Cervical Cancer Cell Lines"; 1999, Journal of Virology, vol. 73, No. 6, pp. 4983-4990.

Ueno, Hikaru et al.; "Adenovirus-Mediated Transfer of Cyclin-dependent Kinase Inhibitor-p21 suppresses Neointimal Formation in the Balloon-Injured Rat Carotid Arteries"; 1995, Annals of the New York Academy of Sciences, pp. 401-411.

Verma et al. (1997) Nature, vol. 389, p. 239.

Wen, S.F. et al.; "Characterization of adenovirus p21 gene transfer, biodistribution, and immune response after local ocular delivery in New Zealand white rabbits"; 2003, Experimantal Eye Research, vol. 355-365.

Wright, Alan F.; "Gene therapy for the eye"; 1997, Br.J. Ophthalmol, vol. 81, pp. 620-623.

Zegers, Mirjam M.P. et al.; "Pak1 and Pix regulate contact inhibition during epithelial wound healing"; 2003 The Embo Journal, vol. 22, No. 16, pp. 4155-4165.

Xu, Hong .J.; "Strategies for Approaching Retinoblastoma Tumor Suppressor Gene Therapy"; 1997, Adv. Pharmacol. , vol. 40, 369-397.

"Recombinant DNA Advisory Committee, meeting minutes"; 2003, 30 pages.

U.S. Appl. No. 90/007,466, Demers.

Online Medical Dictionary Definition of "skin".

Online Medical Dictionary Definition of "cornea".

Supplementary European Search Report from EP 04812200.6, dated Jun. 8, 2009 (4 pages).

* cited by examiner

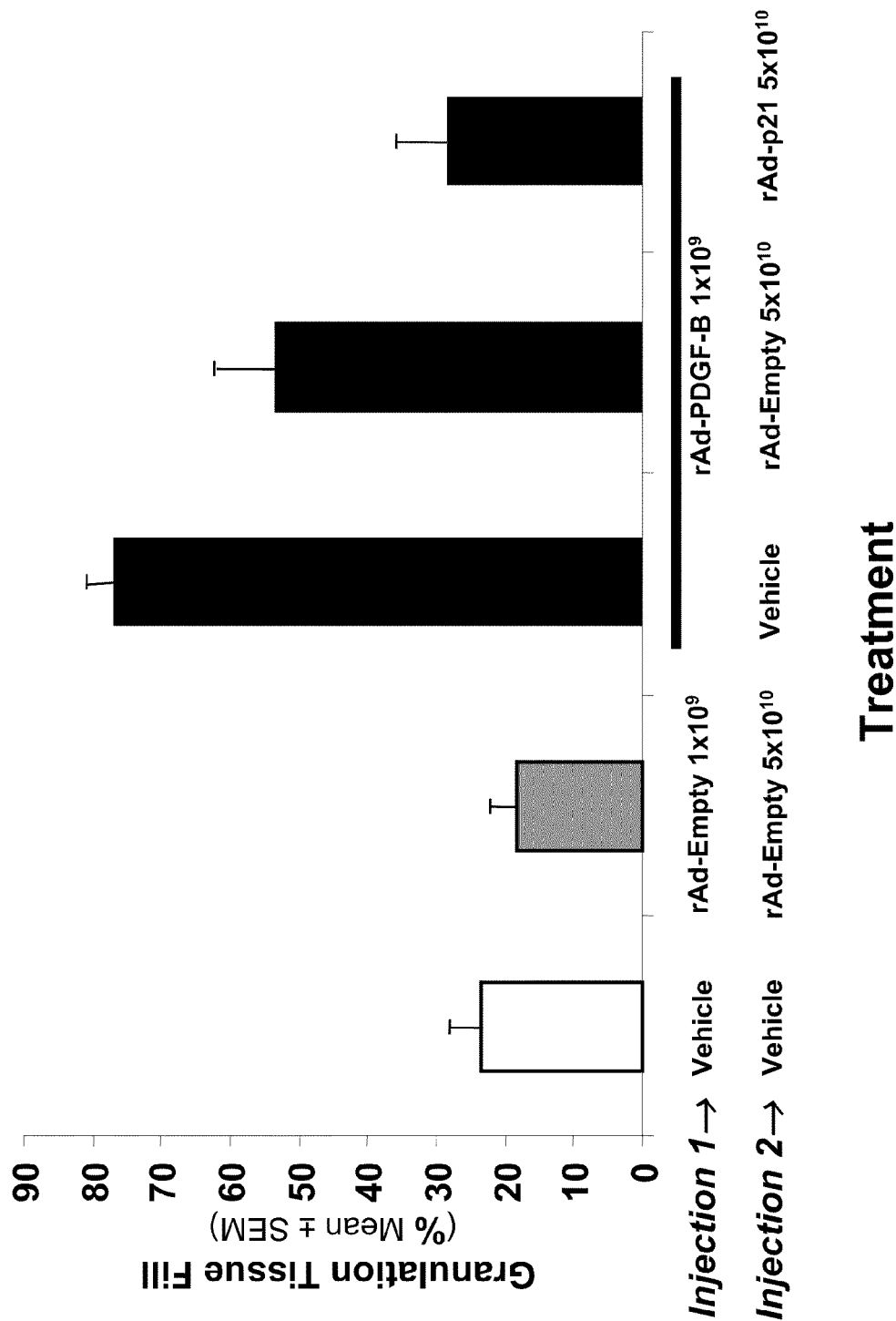

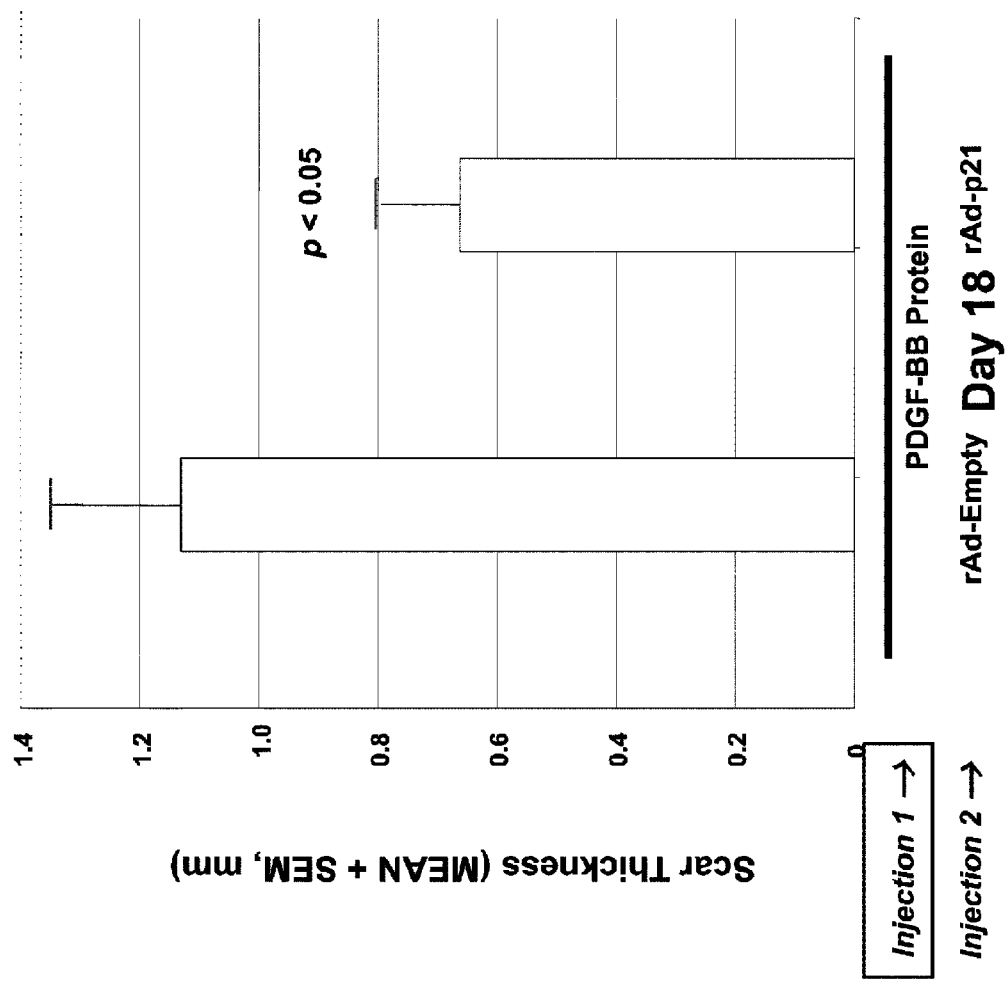

REDUCTION OF DERMAL SCARRING

CROSS-REFERENCE TO RELATED PATENT APPLICATIONS

The present application is a continuation of U.S. patent application Ser. No. 12/268,311, filed Nov. 10, 2008, which is a continuation of U.S. patent application Ser. No. 10/997,769, filed Nov. 23, 2004, now U.S. Pat. No. 7,465,442, issued Dec. 16, 2008, which claims benefit of priority to U.S. Provisional Patent Application No. 60/524,993, filed Nov. 24, 2003, each of which are incorporated by reference for all purposes.

BACKGROUND OF THE INVENTION

Excessive cutaneous scarring is an area of unmet medical need and causes functional, cosmetic and psychological morbidity. See. e.g., Hunt, T. K., *World J Surg,* 4(3): 271-7 (1980); Nicolai, J. P., et al., *Aesthetic Plast Surg,* 11(1):29-32 (1987). Clinical scar management involves consideration of both the continual physical assessment of the scar, including body location and the patient's previous scar history, with a clinical regimen that is often modulated over the course of treatment. Accepted conservative treatments for hypertrophic scars and keloids are limited to surgery, corticosteroid injections, radiotherapy, silicone gel sheeting and pressure therapy. See, e.g., Mustoe, T. A., et al., *Plast Reconstr Surg,* 110(2):560-71 (2002). While scar management has recently experienced new modalities for the physician, scar outcome is still largely unpredictable. Treatments that specifically target the biological mechanisms responsible for hypertrophic scars and keloids would complement existing therapy and could improve current scar outcome.

Cutaneous scarring is described as macroscopic disruptions of normal skin architecture and function, which arise as a consequence of wound repair and proceeds as a fibroproliferative response. See. e.g., Clark, R. A. F., *Wound Repair: Overview and General Considerations,* in THE MOLECULAR AND CELLULAR BIOLOGY OF WOUND REPAIR, (Ed., R. A. F. Clark), 1988, pp. 3-35. The pathogenetic and biological profile of keloids and hypertrophic scars is not fully understood. Keloids are hallmarked by growth beyond the margins of the original trauma site, are associated with familial disposition, and rarely regress. See, e.g., Tredget, E. E., *Ann NY Acad Sci,* 888:165-82 (1999). Hypertrophic scars are raised, erythematous fibrous lesions which usually undergo resolution over time and are associated with contracture of tissue. See, e.g., Tredget, E. E., *Ann NY Acad Sci,* 888:165-82 (1999). While keloids differ from hypertrophic scars in genetic linkage and immunological parameters, both are associated with fibroblast hyperproliferation and excessive extracellular matrix (ECM) deposition. See, e.g., Rockwell, W. B., et al., *Plast Reconstr Surg,* 84(5):827-37 (1989); Tsao, S. S., et al., *Semin Cutan Med Surg,* 21(1):46-75 (2002); Nemeth, A. J., *J Dermatol Surg Oncol,* 19(8):738-46 (1993).

Clearly, scarring remains a problem that is difficult to avoid in many situations. The present invention addresses this and other problems.

BRIEF SUMMARY OF THE INVENTION

The present invention provides methods for reducing scarring. In some embodiments, the methods comprise administering a polynucleotide comprising an expression cassette to skin wherein the expression cassette comprises a promoter operably linked to a polynucleotide encoding $p21^{WAF1/Cip1}$.

In some embodiments, the polynucleotide (optionally in a vector) is administered to a wound on the skin of a subject.

In some embodiments, the DNA is administered as part of a vector. In some embodiments, the vector is a viral vector. In some embodiments, the viral vector is an adenoviral vector. In some embodiments, the adenoviral vector is a replication deficient adenoviral vector.

In some embodiments, the administrating step results in decreased keloids or hypertrophic scarring at the wound compared to scarring on an untreated wound. In some embodiments, the adenoviral vector is administered at a dose of between $10^5$ and $10^7$ particle number (PN) per $cm^2$ of the wound.

In some embodiments, the vector is administered in a biocompatible matrix. In some embodiments, the matrix comprises collagenous, metal, hydroxyapatite, bioglass, aluminate, bioceramic materials, purified proteins or extracellular matrix compositions. In some embodiments, the matrix is a collagen matrix.

In some embodiments, the skin is burned.

The present invention also provides pharmaceutical compositions comprising an expression cassette and a pharmaceutically acceptable excipient, wherein the composition is suitable for topical administration and the expression cassette comprises a promoter operably linked to a polynucleotide encoding $p21^{WAF1/Cip1}$. In some embodiments, the expression cassette (optionally a part of a vector) is within a biocompatible matrix.

In some embodiments, the matrix comprises a viral vector comprising the expression cassette. In some embodiments, the viral vector is an adenoviral vector. In some embodiments, the adenoviral vector is a replication deficient adenoviral vector.

In some embodiments, the matrix comprises collagenous, metal, hydroxyapatite, bioglass, aluminate, bioceramic materials, purified proteins or extracellular matrix compositions. In some embodiments, the matrix is a collagen matrix.

DEFINITIONS

As used herein, "$p21^{WAF1/Cip1}$" refers to the wildtype full length $p21^{WAF1/Cip1}$ protein, active fragments thereof, active variants thereof, and fusions comprising the full-length $p21^{WAF1/Cip1}$ protein or active fragments thereof or active variants thereof, wherein the fusions retain $p21^{WAF1/Cip1}$ activity. The wild type $p21^{WAF1/Cip1}$ protein is a 164 amino acid protein having cell regulatory functions. See, e.g., U.S. Pat. No. 5,302,706. $p21^{WAF1/Cip1}$ is also known in the scientific literature as p21, p21sdi, p21waf1, p21cip1 and p21pic1. The term "$p21^{WAF1/Cip1}$ polynucleotide" refers to polynucleotide sequences encoding $p21^{WAF1/Cip1}$ including, e.g., the human wild-type protein and homologous sequences from other organisms, as well as any mutations or truncations thereof, or fusions that display essentially the same function as the wild-type $p21^{WAF1/Cip1}$ protein.

"$p21^{WAF1/Cip1}$" activity refers to the ability to complement a $p21^{WAF1/Cip1}$ mutation and to act as an inhibitor of cyclin-dependent kinase activity (Harper, J. W., et al. *Cell* 75:805-816 (1993)) and/or inhibit cell-cycle progression. See, e.g., Harper, J. W., et al., supra; Xiong, Y. et al. *Cell* 71:505-514 (1992).

The term "gene" means the segment of DNA involved in producing a polypeptide chain; it includes regions preceding and following the coding region (leader and trailer) as well as intervening sequences (introns) between individual coding segments (exons).

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An "expression cassette" is a nucleic acid, generated recombinantly or synthetically, with a series of specified nucleic acid elements that permit transcription of a particular nucleic acid in a host cell. The expression cassette can be part of a plasmid, virus, or other nucleic acid. Typically, the expression vector includes a promoter operably linked to a nucleic acid to be transcribed.

A "biocompatible matrix" refers to a matrix that does not produce a significant allergic or other adverse reaction in the host subject to which the matrix is administered.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "promoter" or "regulatory element" refers to a region or sequence determinants located upstream or downstream from the start of transcription and which are involved in recognition and binding of RNA polymerase and other proteins to initiate transcription. A "constitutive" promoter is a promoter that is active under most environmental and developmental conditions. An "inducible" promoter is a promoter that is active under environmental or developmental regulation.

BRIEF DESCRIPTION OF THE DRAWINGS

FIG. 3 illustrates rAd-p21$^{WAF1/Cip1}$ treatment effects on granulation tissue fill. PVA sponges were harvested 12 days after implantation (5 days after rAd-p21$^{WAF1/Cip1}$ treatment) and Trichrome stain was performed. Mean percent granulation tissue fill was evaluated by quantitative image analysis as described in Materials and Methods. Comparisons are significant between rAd-PDGF-B/rAd-p21$^{WAF1/Cip1}$ vs. rAd-PDGF-B/vehicle and rAd-PDGF-B/rAd-Empty receiving groups ($p<0.001$ and $p=0.05$, respectively). However, no significant differences were observed between rAd-PDGF-B/rAd-p21$^{WAF1/Cip1}$ vs. vehicle/vehicle and rAd-Empty/rAd-Empty receiving groups ($p>0.3$). N=7 per each treatment group.

FIG. 5 illustrates that p21 expression inhibits elevated scar thickness after the intradermal delivery of rAd-p21 in the rabbit ear excessive scarring model.

DETAILED DESCRIPTION OF THE INVENTION

I. Introduction

Figure 1A:
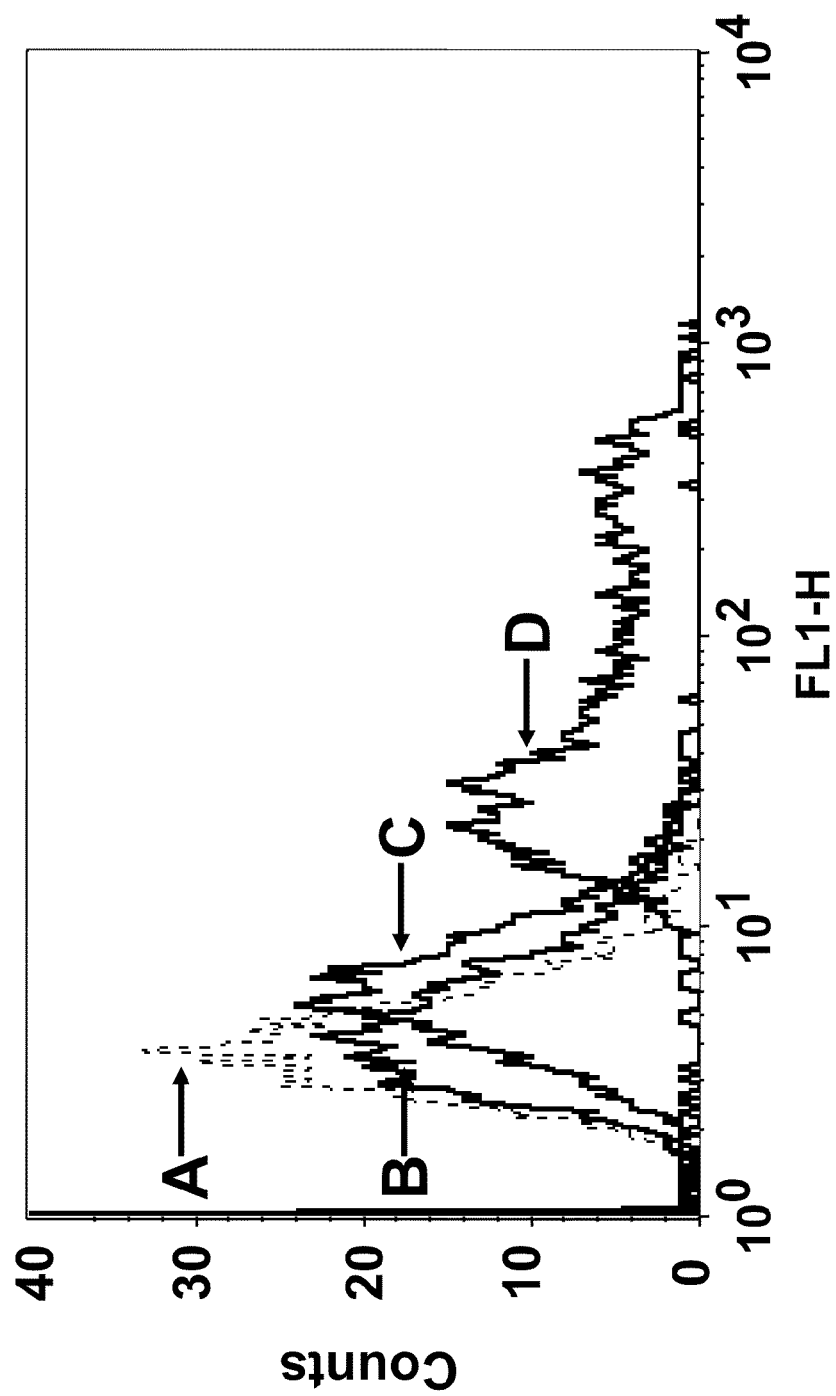
FIG. 1A illustrates Proliferation effects and pro-collagen I protein detection in primary human dermal fibroblast cells after rAd-p21$^{WAF1/Cip1}$ treatment. The figure illustrates expression of p21$^{WAF-1/Cip-1}$ protein in primary human dermal fibroblast cells. Cells were treated for 48 hours with increasing concentrations of rAd, labeled with anti-p21$^{WAF1/CIP1}$-FITC antibody, and analyzed by FACS. In the histogram, line (A, broken line) represents staining on untreated cells. Line (B) represents staining on cells treated with $1\times10^7$ PN/ml rAd-p21$^{WAF1/Cip1}$. Line (C) represents staining on cells treated with $1\times10^8$ PN/ml rAd-p21$^{WAF1/Cip1}$. Line (D) represents staining on cells treated with $1\times10^9$ PN/ml rAd-p21$^{WAF1/Cip1}$ Histogram is representative of 3 experiments.

The present invention provides methods and compositions for reducing and treating scarring in wounded skin. The invention provides that delivery and expression of p21$^{WAF1/Cip1}$ to a wound site reduces the development of granulation tissue and fibroblasts. Without intending to limit the scope of the invention, it is believed that p21$^{WAF1/Cip1}$ inhibits the effect of inflammatory cells (e.g., neutrophils, macrophages and lymphocytes, fibroblasts, etc.) that would otherwise result in undue scarring and cell proliferation during wound healing.

Methods of the invention comprise delivering a polynucleotide encoding a polypeptide comprising p21$^{WAF1/Cip1}$ or an active fragment thereof to a wound site. Expression of p21$^{WAF1/Cip1}$ at the wound site results in wound closure with a reduction of the scarring that would otherwise occur. The invention is particularly useful in preventing or ameliorating hypertrophic scarring and the development and growth of keloids.

II. Wounds

The present invention can be used to reduce scarring from any wounds to the skin. Without limiting the scope of the invention, skin damage resulting from, e.g., burns, punctures, cuts and/or abrasions include wounds that can be treated according to the methods of the invention. The methods of the invention are useful to reduce scarring following surgery, including cosmetic surgery.

Ideally, wounds are treated as soon as possible after the wound has occurred. For example, in some cases, the wound is treated within 72, 48, 24, 18, 12, 6, 3, or 1 hours after the wound occurred. In the case of surgical scars, the methods and compositions of the present invention are administered contemporaneously with the surgery. However, an anti-scarring effect can be realized by treatment after extended periods following the occurrence of the wound. Generally, the amount of p21$^{WAF1/Cip1}$ vector applied to the wounds should be increased the longer the time period between occurrence of the wound and administration of the vector. In the case of replication deficient adenoviral vectors where the gene is under control of a strong constitutive promoter such as the cytomegalovirus immediate early ("CMV") promoter as exemplified herein, the dosage typically ranges from approximately $1\times10^5$ PN/cm$^2$ to $1\times10^9$ PN/cm$^2$, $1\times10^5$ PN/cm$^2$ to $1\times10^8$ PN/cm$^2$, or $1\times10^5$ PN/cm$^2$ to $1\times10^7$ PN/cm$^2$. A typical dose would be approximately $5\times10^6$ PN/cm$^2$. The above reference dose is administered to a wound site immediately (i.e., within a day) after the wound occurred. If the adenoviral vector is applied significantly later (e.g., one week after the wound occurred), increases in the dose of approximately 10-100-fold more vector may be necessary to realize a similar effect. Typical effective p21$^{WAF1/Cip1}$ concentrations in the tissue are approximately 50-150 Units of activity as determined by the WAFT ELISA kit (commercially available from Oncogene Research Products, San Diego, Calif. Cat#QIA18) with a target concentration of approximately 80-100 Units of activity.

Typically, the methods of the invention inhibit or reduce scarring but do not inhibit wound closure. p21$^{WAF1/Cip1}$ can inhibit wound closure if expressed in sufficient amounts. For example, $2\times10^{11}$ PN/cm$^2$ adenoviral vectors comprising p21$^{WAF1/Cip1}$ polynucleotides are sufficient to delay reepithelization in animal models. Additionally, at such doses, effects on the tensile strength of the wound are observed. Thus, it is desirable to use a sufficient amount of a vector comprising a p21$^{WAF1/Cip1}$ polynucleotide to inhibit or reduce scarring while not administrating too much so as to delay re-epithlization or appreciably decrease tensile strength.

III. Gene Delivery

To introduce a polynucleotide sequence encoding p21, it is possible to incorporate a naked plasmid comprising a promoter operably linked to a p21 polynucleotide into cells in a wound. Alternatively, the p21$^{WAF1/Cip1}$ polynucleotide is incorporated into a viral or non-viral delivery system and then introduced into the wound.

1. Non-Viral Delivery Systems

Non-viral delivery systems capable of directing the expression of a p21$^{WAF1/Cip1}$ polynucleotide to the wound include expression plasmids. Expression plasmids are autonomously replicating, extrachromosomal circular DNA molecules, distinct from the normal genome and nonessential for cell survival under nonselective conditions capable of effecting the expression of a DNA sequence in the target cell. Plasmids autonomously replicate in bacteria to facilitate bacterial production, but it is not necessary that such plasmids containing the cyclin dependent kinase gene replicate in the target cell in order to achieve the therapeutic effect. The transgene may also be under control of a tissue specific promoter region allowing expression of the transgene only in particular cell types (e.g., inflammatory cells, including, e.g., neutrophils, macrophages and lymphocytes as well as fibroblasts and keratinocytes). Those of skill in the art will readily appreciate the variety of expression plasmids which may be useful in the practice of the present invention.

The expression plasmid may also contain promoter, enhancer or other sequences aiding expression of a p21 polynucleotide. Although one may use a constitutive promoter such as CMV, it may be useful to employ promoters having specific activity in the target cells such as pFascin (Sudowe, et al. Molecular Therapy 8(4):567 (2003)) and the keratin-12 promoter (Ikawa, et al., Molecular Therapy 8(4):666 (2003). Inducible promoters which are functional under certain conditions in response to chemical or other stimuli may also be employed to effectively control expression of p21$^{WAF1/Cip1}$ Examples of inducible promoters are known in the scientific literature. See, e.g., Yoshida and Hamada, Biochem. Biophys. Res. Comm. 230:426-430 (1997); Iida, et al., J. Virol. 70(9): 6054-6059 (1996); Hwang, et al., J. Virol 71(9):7128-7131 (1997); Lee, et al., Mol. Cell. Biol. 17(9):5097-5105 (1997); and Dreher, et al., J. Biol. Chem. 272(46):29364-29371 (1997). An example of radiation inducible promoters include the EGR-1 promoter. See, e.g., Boothman, et al. (1994) volume 138 supplement pages S68-S71

Additional genes, such as those encoding drug resistance, can be included to allow selection or screening for the presence of the recombinant vector. Such additional genes can include, for example, genes encoding neomycin resistance, multi-drug resistance, thymidine kinase, beta-galactosidase, dihydrofolate reductase (DHFR), and chloramphenicol acetyl transferase.

The expression plasmid containing $p21^{WAF1/Cip1}$ polynucleotide may be encapsulated in liposomes. Liposomes include emulsions, foams, micelles, insoluble monolayers, liquid crystals, phospholipid dispersions, lamellar layers and the like. The delivery of DNA sequences to target cells using liposome carriers is well known in the art. A variety of methods are available for preparing liposomes, as described in, e.g., Szoka et al. *Ann. Rev. Biophys. Bioeng.* 9:467 (1980), U.S. Pat. Nos. 4,394,448; 4,235,871; 4,501,728; 4,837,028; and 5,019,369. Liposomes useful in the practice of the present invention may be formed from one or more standard vesicle-forming lipids, which generally include neutral and negatively charged phospholipids and a sterol, such as cholesterol.

Examples of such vesicle forming lipids include DC-chol, DOGS, DOTMA, DOPE, DOSPA, DMRIE, DOPC, DOTAP, DORIE, DMRIE-HP, n-spermidine cholesterol carbamate and other cationic lipids as disclosed in U.S. Pat. No. 5,650,096. The selection of lipids is generally guided by consideration of, e.g., liposome size, acid lability and stability of the liposomes in the blood stream. Additional components may be added to the liposome formulation to increase serum half-life such as polyethylene glycol coating (so called "PEGylation") as described in U.S. Pat. Nos. 5,013,556 and 5,213,804.

In order to facilitate delivery of the therapeutic gene to a particular tissue or organ, it may be advantageous to incorporate elements into the non-viral delivery system which facilitate cellular targeting.

2. Viral Delivery Systems

In other instances, the DNA sequence is delivered by a viral delivery system wherein the $p21^{WAF1/Cip1}$ polynucleotide is incorporated into a viral genome capable of infecting the target cell and the $p21^{WAF1/Cip-1}$ polynucleotide is operably linked to expression and control sequences such that the polynucleotide is expressed under appropriate conditions in the target cell. The vectors useful in the practice of the present invention may also be derived from the viral genomes. Vectors which may be employed include recombinantly modified enveloped or non-enveloped DNA and RNA viruses, preferably selected from baculoviridiae, parvoviridiae, picornaviridiae, herpesveridiae, poxyiridae or adenoviridiae. Chimeric vectors may also be employed which exploit advantageous elements of each of the parent vector properties. See, e.g., Feng, et al. *Nature Biotechnology* 15:866-870 (1997). Such viral genomes may be modified by recombinant DNA techniques to include a $p21^{WAF1/Cip1}$ polynucleotide and may be engineered to be replication deficient, conditionally replicating or replication competent. Typically, the vectors are replication deficient or conditionally replicating. Exemplary vectors are derived from the adenoviral, adeno-associated viral and retroviral genomes. In some embodiments, the vectors are replication incompetent vectors derived from the human adenovirus genome. The transgene may also be under control of a tissue specific promoter region allowing expression of the transgene only in particular cell types.

In other instances, to insure efficient delivery of the $p21^{WAF1/Cip1}$ polynucleotide to a particular tissue or organ, it may be advantageous to incorporate elements into the viral delivery system which facilitate cellular targeting. Viral envelopes used for packaging the constructs of the invention can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis. See, e.g., Curiel, et al. *Proc. Natl. Acad. Sci. U.S.A.* 88:8850-8854 (1991). Cell type specificity or cell type targeting may also be achieved in vectors derived from viruses having characteristically broad infectivities by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham, et al. *J. Virol.* 71 (11):8221-8229 (1997) (incorporation of RGD peptides into adenoviral fiber proteins); Arnberg, et al. *Virology* 227:239-244 (1997) (modification of adenoviral fiber genes to achieve tropism to the eye and genital tract); Harris and Lemoine *TIG* 12(10):400-405 (1996); Stevenson, et al., *J. Virol.* 71(6):4782-4790 (1997); Michael, et al. *Gene Therapy* 2:660-668 (1995) (incorporation of gastrin releasing peptide fragment into adenovirus fiber protein); and Ohno, et al. *Nature Biotechnology* 15:763-767 (1997) (incorporation of Protein A-IgG binding domain into Sindbis virus); and U.S. Pat. Nos. 5,721,126 and 5,559,099. Other methods of cell specific targeting have been achieved by the conjugation of antibodies or antibody fragments to the envelope proteins. See, e.g., Michael, et al. *J. Biol. Chem.* 268:6866-6869 (1993), Watkins, et al. *Gene Therapy* 4:1004-1012 (1997); Douglas, et al. *Nature Biotechnology* 14:1574-1578 (1996). Alternatively, particular moieties may be conjugated to the viral surface to achieve targeting. See, e.g., Nilson, et al. *Gene Therapy* 3:280-286 (1996) (conjugation of EGF to retroviral proteins).

Conditionally replicating viral vectors are used to achieve selective expression in particular cell types while avoiding untoward broad spectrum infection. Examples of conditionally replicating vectors are described in Bischoff, et al. *Science* 274:373-376 (1996); Pennisi, E., *Science* 274:342-343 (1996); Russell, S. J. *Eur. J. of Cancer* 30A(8):1165-1171 (1994).

In some instances, particularly when employing a conditionally replicating or replication competent vector, it may be desirable to include a suicide gene in the viral vector in addition to the p21WAF1/Cip1 polynucleotides. A suicide gene is a nucleic acid sequence, the expression of which renders the cell susceptible to killing by external factors or causes a toxic condition in the cell. A well known example of a suicide gene is the thymidine kinase (TK) gene (see, e.g., U.S. Pat. No. 5,631,236 and U.S. Pat. No. 5,601,818) in which the cells expressing the TK gene product are susceptible to selective killing by the administration of gancyclovir. This provides a "safety valve" to the viral vector delivery system to prevent widespread infection due to the spontaneous generation of fully replication competent viral vectors of broad range infectivity.

In some embodiments of the invention, the vector is derived from genus adenoviridiae. Particularly preferred vectors are derived from the human adenovirus type 2 or type 5. Such vectors are typically replication deficient by modifications or deletions in the E1a and/or E1b coding regions. Other modifications to the viral genome to achieve particular expression characteristics or facilitate repeat administration or lower immune response are preferred.

In some embodiments, the recombinant adenoviral vectors have complete or partial deletions of the E4 coding region, optionally retaining (or deleting) E4 ORF6 and ORF 6/7. The E3 coding sequence has been demonstrated to be nonessential and may be deleted from adenoviral vectors but is preferably retained. In some embodiments, the promoter operator region of E3 be modified to increase expression of E3 to achieve a more favorable immunological profile for the therapeutic vectors. In some embodiments, the vector used is a human adenoviral type 5 vector containing a p21WAF1/Cip1 polynucleotide under control of the cytomegalovirus promoter region and the tripartite leader sequence having E3 under control of the CMV promoter and deletion of E4 coding regions while retaining E4 ORF6 and ORF 6/7.

In some embodiments, the adenovirus expression vector comprises a partial or total deletion of protein IX. See, e.g., U.S. Patent Publication No. 2003/0091534. Other adenoviral vectors include those described in, e.g. U.S. Patent Publication Nos. 2003/0192066 and 2003/0157688.

IV. Pharmaceutical Formulation

The invention further provides pharmaceutical formulations comprising the p21WAF1/Cip1 polynucleotide in a viral or non-viral delivery system for administration. The compositions of the invention will be formulated for administration by manners known in the art acceptable for administration to a mammalian subject, preferably a human. In particular delivery systems may be formulated for topical administration.

The compositions of the invention can be administered in topical formulations or polymer matrices, hydrogel matrices, polymer implants, or encapsulated formulations to allow slow or sustained release of the compositions. Any biocompatible matrix material containing DNA encoding $p21^{WAF1/Cip1}$ can be formulated and used in accordance with the invention.

The gene activated matrices of the invention may be derived from any biocompatible material. Such materials may include, but are not limited to, biodegradable or non-biodegradable materials formulated into scaffolds that support cell attachment and growth, powders or gels. Matrices may be derived from synthetic polymers or naturally occurring proteins such as collagen, other extracellular matrix proteins, or other structural macromolecules.

The type of matrix that may be used in the compositions, devices and methods of the invention is virtually limitless and may include both biological and synthetic matrices. The matrix will have all the features commonly associated with being "biocompatible", in that it is in a form that does not produce an adverse, allergic or other untoward reaction when administered to a mammalian host. Such matrices may be formed from natural or synthetic materials. The matrices will typically be biodegradable. The matrices may take the form of sponges, implants, tubes, Telfa® pads, Band-Aid® brand adhesive bandages, bandages, pads, lyophilized components, gels, patches, artificial skins, powders or nanoparticles. In addition, matrices can be designed to allow for sustained release and/or to provide a framework into which cells may migrate and be transduced and to provide a structural framework to facilitate healing.

Biocompatible biodegradable polymers that may be used are well known in the art and include, by way of example and not limitation, polyesters such as polyglycolides, polylactides and polylactic polyglycolic acid copolymers ("PLGA") (Langer and Folkman, Nature 263:797-800 (1976); polyethers such as polycaprolactone ("PCL"); polyanhydrides; polyalkyl cyanoacrylates such as n-butyl cyanoacrylate and isopropyl cyanoacrylate; polyacrylamides; poly(orthoesters); polyphosphazenes; polypeptides; polyurethanes; and mixtures of such polymers. Also polymers of polyethylene glycol (PEG), cyclodextrins and derivatized cyclodextrins, and collagen (whether obtained from natural sources of recombinant) may also be employed.

One method to control the release of nucleic acids from the matrix involves controlling the molecular weight of the polymer as well as chemical composition of the matrix. For example, for PLGA matrices the composition ratio of lactic acid/glycolic acid affects the release period. Generally, a higher ratio of lactic acid/glycolic acid, such as for example 75/25, will provide for a longer period of controlled of sustained release of the nucleic acids, whereas a lower ratio of lactic acid/glycolic acid will provide for more rapid release of the nucleic acids.

Another particular example of a suitable material is fibrous collagen, which may be lyophilized following extraction and partial purification from tissue and then sterilized. Matrices may also be prepared from tendon or dermal collagen, as may be obtained from a variety of commercial sources, such as, e.g., Sigma and Collagen Corporation. Collagen matrices may also be prepared as described in U.S. Pat. Nos. 4,394,370 and 4,975,527.

In addition, lattices made of collagen and glycosaminoglycan (GAG) such as that described in U.S. Pat. No. 4,505,266 or U.S. Pat. No. 4,485,097, may be used in the practice of the invention. The collagen/GAG matrix may effectively serve as a support or "scaffolding" structure into which repair cells may migrate. Collagen matrix, such as those disclosed in U.S. Pat. No. 4,485,097, may also be used as a matrix material.

Prior to the application of the matrices to the wound site, damaged skin or devitalized tissue may be removed. The matrices of the invention can contain additional factors or compounds that improve wound healing as well as minimizing inflammation, infection and/or hyperproliferative responses. Examples of such agents include silver nitrate and antibiotics.

V. Carriers

When the delivery system is formulated as a solution or suspension, the delivery system is in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the compositions of the invention in the pharmaceutical formulations can vary widely, i.e., from less than about 0.01%, usually at or at least about 2% to as much as 20% to 50% or more by volume, and will be selected primarily by fluid volumes, viscosities, etc., in accordance with the particular mode of administration selected.

VII. Delivery Enhancers

The pharmaceutical formulations of the invention may optionally include one or more delivery-enhancing agents.

The term "delivery enhancing agents" includes agents which facilitate the transfer of the nucleic acid or protein molecule to the target cell. Examples of such delivery enhancing agents include detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol as described in U.S. Pat. No. 5,789,244, the entire teaching of which is herein incorporated by reference. Glycols include glycerine, propyleneglycol, polyethyleneglycol and other low molecular weight glycols such as glycerol and thioglycerol.

Acetates such as acetic acid, gluconic acid, and sodium acetate are further examples of delivery-enhancing agents.

Examples of surfactants are sodium dodecyl sulfate (SDS) and lysolecithin, polysorbate 80, nonylphenoxypolyoxyethylene, lysophosphatidylcholine, polyethyleneglycol 400, polysorbate 80, polyoxyethylene ethers, polyglycol ether surfactants and DMSO. Bile salts such as taurocholate, sodium tauro-deoxycholate, deoxycholate, chenodeoxycholate, glycocholic acid, glycochenodeoxycholic acid and other astringents like silver nitrate may be used. Heparin-antagonists like quaternary amines such as protamine sulfate may also be used. Cyclooxygenase inhibitors such as sodium salicylate, salicylic acid, and non-steroidal antiinflammatory drug (NSAIDS) like indomethacin, naproxen, diclofenac may be used.

SYN3 is a surfactant-like molecule that enhances gene delivery and is described in U.S. Pat. No. 6,392,069, the entire teaching of which is herein incorporated by reference for all purposes. Additional compounds are also described in U.S. Patent Publication No. 2003/0170216, herein incorporated by reference.

The delivery of genes may also be enhanced by the use of detergents as described in U.S. Pat. No. 6,165,779, the entire teaching of which is herein incorporated by reference. Detergents include anionic, cationic, zwitterionic, and nonionic detergents. Exemplary detergents include but are not limited to taurocholate, deoxycholate, taurodeoxycholate, cetylpyridium, benalkonium chloride, ZWITTERGENT™ 3-14 detergent, CHAPS (3-{(3-Cholamidopropyl)dimethylammoniol}-1-propanesulfonate hydrate, Aldrich), Big CHAP, Deoxy Big CHAP, TRITON™-X-100 detergent, C12E8, Octyl-B-D-Glucopyranoside, PLURONIC™-F68 detergent, TWEEN™ 20 detergent, and TWEEN™ 80 detergent (CAL-BIOCHEM™ Biochemicals).

The concentration of the delivery-enhancing agent will depend on a number of factors known to one of ordinary skill in the art such as the particular delivery-enhancing agent being used, the buffer, pH, target tissue or organ and mode of administration. The concentration of the delivery-enhancing agent will be in the range of 1% to 50% (v/v), preferably 10% to 40% (v/v) and most preferably 15% to 30% (v/v).

Phosphate buffered saline (PBS) is a possible solubilizing agent for these compounds. However, one of ordinary skill in the art will recognize that certain additional excipients and additives may be desirable to achieve solubility characteristics of these agents for various pharmaceutical formulations. For example, the addition of well known solubilizing agents such as detergents, fatty acid esters, surfactants may be added in appropriate concentrations so as to facilitate the solubilization of the compounds in the various solvents to be employed. When the solvent is PBS, a preferred solubilizing agent is Tween 80 at a concentration of approximately 0.15%.

These delivery-enhancing compounds may be used alone, in combination with each other, or in combination with another delivery-enhancing agent.

EXAMPLES

Example 1

We demonstrate that rAd-p21$^{WAF1/Cip1}$ can effectively attenuate proliferation of human primary fibroblasts and procollagen type I deposition. Additionally, we demonstrate that rAd-p21$^{WAF1/Cip1}$ attenuates granulation tissue and ECM deposition in a rat PVA sponge wound healing model. Our results suggest that exogenous expression of p21$^{WAF-1/Cip-1}$ is a therapeutic option to modulate excessive scarring.

Methods and Materials

Recombinant adenovirus vector construction and purification. The recombinant adenovirus containing human p21$^{WAF-1/Cip-1}$ has previously been described (Perkins, T. W., et al., *Arch Ophthalmol.* 120(7): 941-9 (2002)). Briefly, the p21$^{WAF-1/Cip-1}$ encoding region under the control of the constitutive cytomegalovirus immediate early promoter (CMV) was cloned into an E1/partial E3 deleted recombinant adenovirus using methods described in Wills et. al., *Hum Gene Ther.* 5(9):1079-88 (1994). The rAd-Empty control adenoviral vector was constructed in similar format as rAd-p21$^{WAF1/Cip1}$ except a transgene was not engineered into the expression cassette. rAd-PDGF-B is an E1/parital E3 deleted adenovirus vector containing a CMV-PDGF-B expression cassette, cloned in the E1-deletion site. The PDGF-B cDNA was PCR amplified from a human placental cDNA library (Clonetech, Palo Alto, Calif.), and 100% homology was confirmed by sequence alignment to Genbank clone M12738. This cDNA was cloned into an adenovirus E1 transfer plasmid containing a CMV promoter and an E1BpIXpoly-A expression cassette. Homologous recombination in *E. coli* strain BJ5183 by the method of Chartier et al. was used to generate infectious viral DNA which was subsequently transfected into human kidney 293 cells to generate and propagate virus (Chartier, C., et al., *J Virol,* 70(7):4805-10 (1996)). Virus particles were purified by column chromatography (Shabram, P. W., et al., *Hum Gene Ther,* 8(4):453-65 (1997)), quantified, and dosed by particle number (PN) based upon guidance from the Food and Drug Administration (Guidance for Human Somatic Cell Therapy and Gene Therapy, Center for Biologics Evaluation and Research, March 1998).

Cells. Normal adult human dermal fibroblast cells were obtained from Cambrex Bio Science (Rutherford, N.J.) and maintained in recommended growth media. Experiments were performed with cells at passage number ≦4.

Adenovirus infections and bromodeoxyuridine pulse-labeling of cells. Cells were synchronized in G0/G1 by plating in Fetal Bovine Serum (FBS) deficient media for two days and were subsequently treated with varying doses ($1 \times 10^8$-$3 \times 10^9$ PN/ml) of either rAd-p21WAF1/Cip1 or rAd-Empty in FBS deficient media. After 24 hrs, media was removed and media containing 20% FBS was added to release cells from G0/G1 arrest. Cells were pulse-labeled at 24 hours post-release with 10 μM bromodeoxyuridine (BrdU; Boeheringer-Mannheim, Indianapolis, Ind.) for 4 hours and harvested for bivariate BrdU/DNA flow cytometric analysis by fixation in 70% ethanol, followed by digestion with 0.08% pepsin for 30 min at 37° C. Cells were centrifuged at 1500 RPM, resuspended in 2 N HCl and incubated at 37° C. for 20 minutes. 1 M sodium borate was added and cells were washed in IFA/Tween 20 (0.01 M HEPES, 0.005% sodium azide, 0.5% Tween 20, 5% FBS, 0.15 M NaCl), and incubated for 30 minutes with a 1:10 dilution of anti-BrdU antibody (Becton-Dickinson, Franklin Lakes, N.J.) without Tween 20. Finally, cells were washed in IFA/Tween 20, incubated in IFA/Tween 20/RNase for 15 minutes at 37° C., stained with propidium iodide (50 μg/ml) and analyzed on the FL-1 channel by a FACS can flow cytometer (Becton Dickinson) using the CellQuest (Becton Dickinson) software.

Enzyme linked immunoassay for detection of human procollagen type 1 C-peptide (PIP). Cells were plated in complete media containing 10% FBS, grown to confluency and infected with adenovirus constructs in media deficient of FBS for 24 hours. Cells were then washed and cultured for 24 hours in media without FBS prior to PIP analysis. Detection of PIP was evaluated by ELISA (TaKaRa Bio Inc., Japan) on cell lysates with $1 \times 10^6$ cells, according to the manufacturers instructions.

$p21^{WAF-1/CIP-1}$ detection by FACS. Cells were fixed in 75% ethanol/PBS for 30 minutes at 4° C. and blocked for non-specific antibody binding with 0.1% BSA/PBS at 37° C. for 30 minutes. 2 μg/ml anti-$p21^{WAF-1/CIP-1}$ antibody conjugated with FITC (Ab-1, Oncogene, San Diego, Calif.) was incubated with cells for 60 minutes at room temperature. Cells were washed in 0.1% BSA, resuspended in PBS and analyzed by FACS on the FL-1 channel.

PVA sponge model. Animal care and experiments were conducted in accordance with the National Institutes of Health Guide for the Care and Use of Laboratory Animals and were approved by appropriate review committees. Male Sprague-Dawley rats (Harlan, Indianapolis, Ind.) weighing 350-400 grams, were anesthetized with ketamine/xylazine and six full thickness, 5 mm linear incisions were made on the ventral surface of each rat. A single sterile polyvinyl alcohol (PVA) sponge (Grade 3: 12.7 mm×3 mm; M-PACT, Eudora, Kans.) was inserted subcutaneously into each incision and closed with wound clips. Four days after sponge implantation, $1 \times 10^9$ PN of rAd-PDGF-B or rAd-Empty formulated in 200 μl of collagen solution (Cohesion Technologies, Palo Alto, Calif.) or 200 μl vehicle control were injected into the interior of each sponge. Three days after the first injections, $1 \times 10^9$, $1 \times 10^{10}$ or $5 \times 10^{10}$ PN of rAd-p21$^{WAF1/Cip1}$ formulated in 100 μl of vPBS (PBS, 3% sucrose v/v) was injected into each sponge. Animals were euthanized 5 days after the second injection and central portions of each sponge were harvested, fixed in 4% paraformaldehyde, paraffin embedded, and sectioned 6-μm thick. For proliferative index studies, 50 mg/kg of BrdU (Calbiochem-Novabiochem Corp., San Diego, Calif.) was injected into rats intraperitoneally 24 hours prior to euthanasia.

Immunohistochemistry. For $p21^{WAF-1/Cip-1}$ protein detection, 6-μm, PVA sponge paraffin sections were immersed in −20° C. ethanol/acetic acid (2:1) for 10 minutes, followed by antigen retrieval in high pH buffer (Dako, Carpinteria, Calif.) with steam for 20 minutes. Endogenous peroxidase was quenched by incubation with 3% (v/v) $H_2O_2$. Slides were blocked in 20% (v/v) goat serum and then incubated with mouse monoclonal anti-human $p21^{WAF-1/Cip-1}$ (1:100, BD-PharMingen, San Diego, Calif.) antibody for one hour. After washing in PBS (3×5 minutes), slides were incubated with biotinylated goat anti-mouse IgG secondary antibody (1:200, Zymed, San Francisco, Calif.) for 30 minutes. Slides were rinsed in PBS (3×5 minutes), incubated with Steptavidin/HRP conjugate (Dako) for 10 minutes and developed with AEC chromagen/substrate (Dako) followed by a hematoxylin counterstain. For BrdU detection, a combined protocol and reagents from Zymed's BrdU staining kit and Vectastain Elite ABC kit (Vector Labs, Burlingame, Calif.,) was used. Briefly, tissue sections were placed on sialyted glass slides and microwaved at 50% power for 5 minutes. Sections were steamed for 20 minutes in pre-heated citrate buffer (pH 6.0), rinsed, and endogenous peroxidase was quenched with 3% (v/v) $H_2O_2$ for 10 minutes. The Zymed kit protocol was followed up to and including incubation with biotinylated mouse anti-BrdU primary antibody. Slides were subsequently rinsed in PBS, incubated with Vectastain Elite ABC reagent for 30 minutes, rinsed again and developed with Vector Nova red chromagen/substrate (Vector Labs) for 5-15 minutes. For Ki67 detection, paraffin tissue sections were microwaved at maximum power in 10 mM citrate buffer (pH 6.0), washed in PBS (3×5 minutes) and blocked with 20% (v/v) goat serum for 30 minutes. Sections were incubated with mouse anti-human Ki67 (1:100; PharMingen) primary antibody for 1 hour, rinsed in PBS (3×5 minutes) and reacted with a 1:200 dilution of biotinylated goat anti-mouse IgG (PharMingen) for 30 minutes. Diaminobenzidine (DAB; Vector Labs) was used for chromagen detection of Ki67 positive cells per kit instructions followed by counterstain with hematoxylin.

Quantitative image analysis. To evaluate the extent of granulation tissue fill, histological sections of PVA sponges were processed using Masson Trichrome staining method. Computer-assisted quantitative analysis was performed using Image Pro Plus™ software (Media Cybernetics, Silver Spring, Md.) with calibrated digital photographs acquired with a Nikon E600 microscope and a 4× Plan-Fluor objective (Nikon USA, Melville, N.Y.). Analysis consisted of quantifying granulation tissue area within the interior of the sponge divided by the entire sponge area interior multiplied by 100 for percent granulation tissue fill. Sample size consisted on average of 6 sponges per treatment group. For proliferative index in vivo, images from BrdU and Ki67 immunohistochemical sections were digitally acquired with a 40× or 4× microscope objective and imported into Adobe Photoshop 5.0 software (Adobe Systems Inc., San Jose, Calif.). Positive cell counts (red or brown) and total cell counts (purple nuclei) were scored for each field observed. For BrdU, three-400X fields (minimum of 1500 cells) per tissue section were counted from each group. For Ki67, 3 entire tissue sections per group (minimum of 13,000 cells/section) were evaluated. Nuclear staining of BrdU or Ki67 regardless of staining intensity, was considered positive. Percent proliferative index was calculated by dividing the red or brown cell population count by the red or brown plus purple cell population multiplied by 100.

Statistical analyses. Data are presented as arithmetic means±SD or ±SEM, where noted. Statistical analysis of data was conducted using unpaired student t-test (StatView, SAS Institute Inc, Cary, N.C.). Differences were considered significant at $p \leq 0.05$ Results Human Dermal Fibroblast Cells Express Exogenous $p21^{WAF-1/Cip-1}$ Protein and Exhibit Cell Cycle Arrest in Response to rAd-p21$^{WAF1/Cip1}$ $p21^{WAF-1/Cip-1}$ gene expression was assessed in human primary dermal fibroblasts cells treated with increasing doses of rAd-p21$^{WAF1/Cip1}$, or rAd-Empty for 48 hours. In response to rAd-p21$^{WAF1/Cip1}$ but not rAd-Empty, the expression of $p21^{WAF-1/Cip-1}$ increased in a dose dependent manner, as determined by FACS analysis (FIG. 1A). In response to $1 \times 10^8$ PN/ml, p21$^{WAF1/Cip1}$ expression increased over untreated cells from 4.1±1.0 (untreated) to 6.0±0.2 (p=0.005). In response to the highest dose of $1 \times 10^9$ PN/ml rAd-p21$^{WAF1/Cip1}$ expression increased over untreated cells from 4.1±1.0 to 35.1±1.5 (p=0.001). Therefore, $p21^{WAF-1/Cip-1}$ could be efficiently expressed in primary dermal fibroblasts in a dose dependent manner.

Figure 1B:
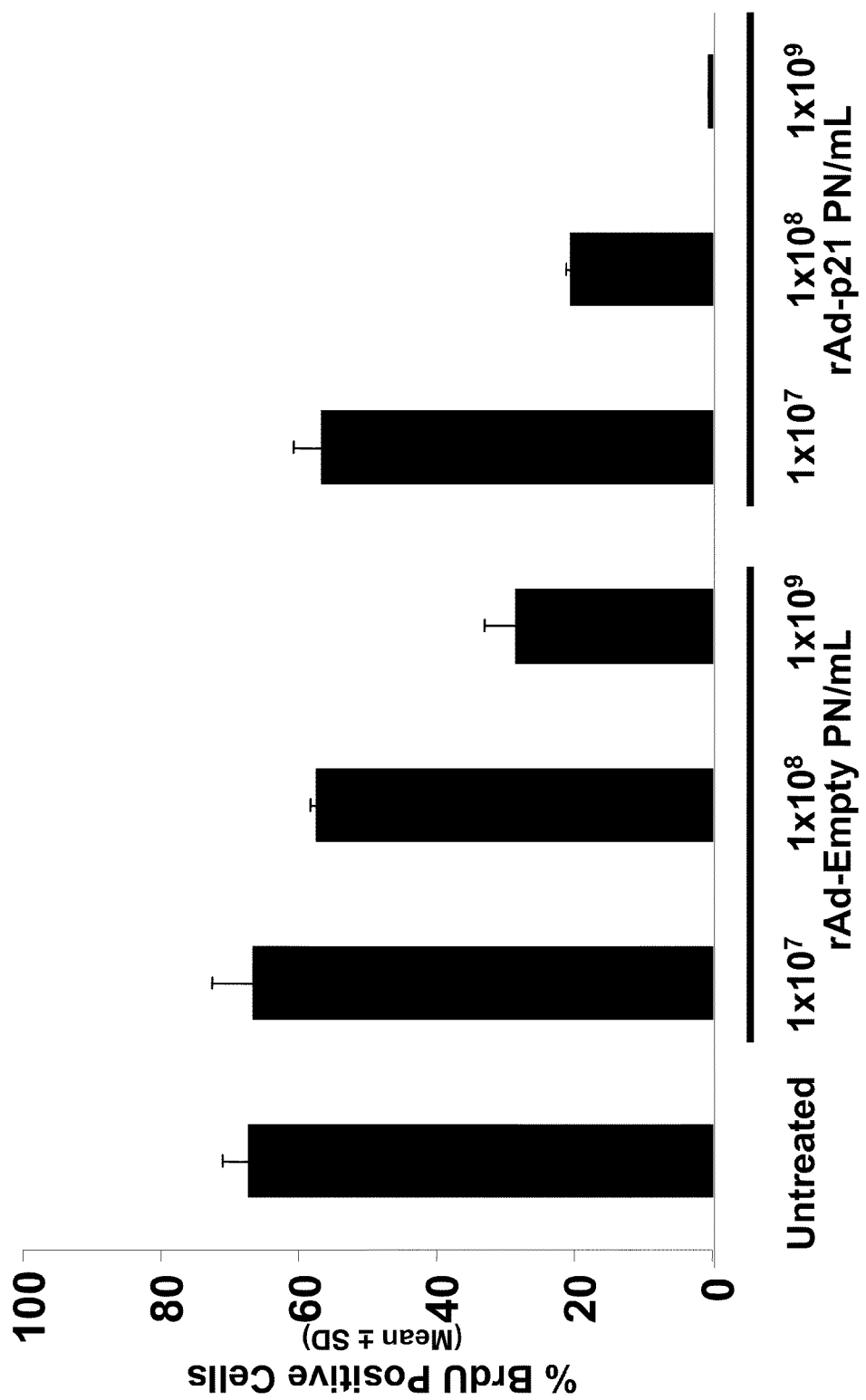
FIG. 1B illustrates cell cycle arrest following administration of various adenoviral vectors. Cells were treated for 48 hours with increasing concentrations of rAd (X-axis), pulse-labeled with BrdU and analyzed by FACS. Data are plotted on the Y-axis as percentage of cells incorporating BrdU (closed histograms). Each bar represents the mean of triplicate wells ±one standard deviation. Comparisons are significant between rAd-Empty at doses of $1\times10^8$ and $1\times10^9$ PN/ml and rAd-p21$^{WAF1/Cip1}$ treatment group ($p<0.05$).

Next, we performed in vitro dose response studies to determine if exogenous $p21^{WAF-1/Cip-1}$ expression could induce cell cycle arrest in human dermal fibroblasts. Cells treated with $1 \times 10^7$ to $1 \times 10^9$ PN/ml rAd-p21$^{WAF1/Cip1}$ showed a dose dependent reduction in cell proliferation as measured by BrdU incorporation and FACS analysis (FIG. 1B). The percent of cells in S-phase decreased from an average of 64.4±5.7% in the untreated cell population, to 20.6±2.6% in response to $1\times10^8$ PN/ml of rAd-p21$^{WAF1/Cip1}$. At the highest dose of rAd-p21$^{WAF1/Cip1}$, $1\times10^9$ PN/ml, a decrease in percent of cells in S-phase was observed with only 0.6±0.1% positive cells detected. Detectable cell cycle inhibition was observed with rAd-Empty at the two highest doses. Specifically, at $1\times10^8$ PN/ml of rAd-Empty, 56.9±1.0% of cells incorporated BrdU, while at $1\times10^9$ PN/ml, 34.4±10.7% of cells incorporated BrdU. Attenuation of proliferation in response to high doses of control adenoviruses has been previously described (Brand, K., et al., *Gene Ther,* 6(6):1054-63 (1999)). BrdU incorporation was significantly reduced when rAd-p21$^{WAF1/Cip1}$ was compared to rAd-Empty at $1\times10^8$ and $1\times10^9$ PN/ml (p<0.05). These data suggest that while high doses of recombinant adenovirus treatment induce general anti-proliferative effects, we have demonstrated a p21$^{WAF1/Cip1}$-specific dose dependent reduction in proliferative response with rAd-p21$^{WAF1/Cip1}$ in wound target cells.

Human Dermal Fibroblast Cells Decrease Production of PIP in Response to rAd-p21$^{WAF1/Cip1}$.

Figure 1C:
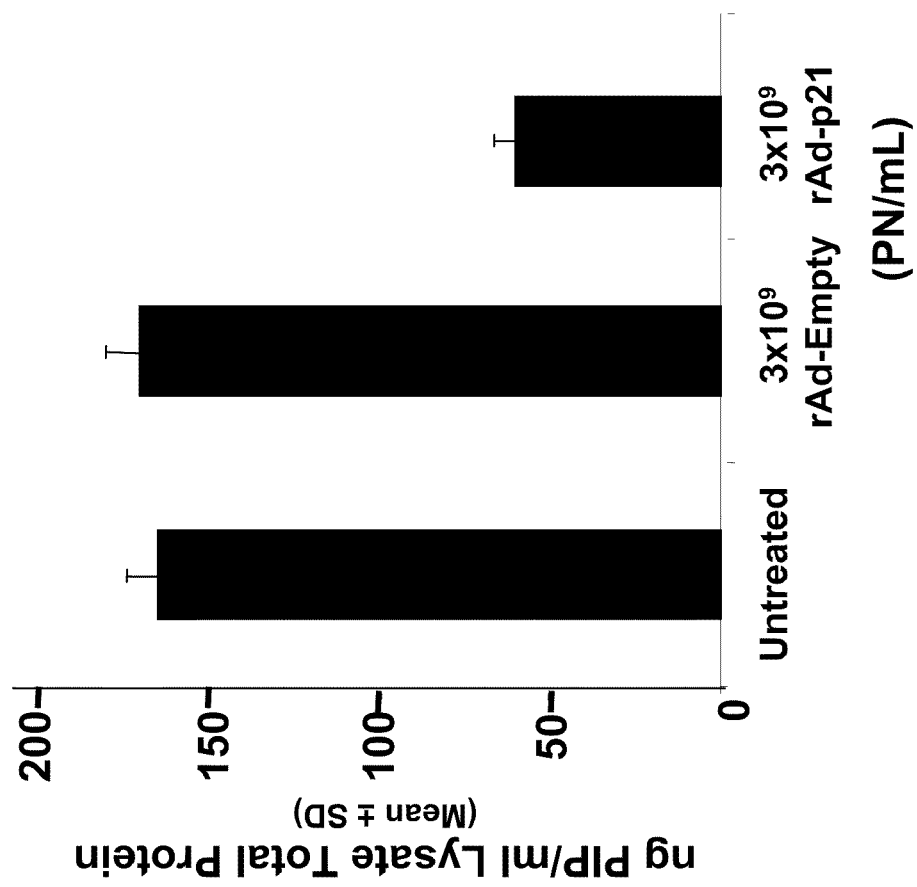
FIG. 1C illustrates PIP protein levels following administration of various adenoviral vectors. Cells were incubated for 48 hours with increasing concentrations of recombinant adenovirus (X-axis). Cell lysates were harvested and analyzed for PIP by ELISA. Data are plotted as ng of PIP per ml of total lysate protein (Y-axis). Each bar represents the mean of triplicate wells ±one standard deviation. Comparisons are significant between $3\times10^9$ PN/ml rAd-p21$^{WAF1/Cip1}$ treatment group and all other groups ($p<0.05$).

To determine if the PIP peptide was reduced after delivery of p21$^{WAF1/Cip1}$, human dermal fibroblasts were treated with increasing doses of rAd-p21$^{WAF1/Cip1}$, or rAd-Empty for 48 hours (FIG. 1C). ELISAs on lysates from equal number of cells were performed to quantify intracellular PIP levels. The data showed greater then 2-fold reduction in PIP after human dermal fibroblasts were treated with rAd-p21$^{WAF1/Cip1}$ as compared to control groups. A decrease in PIP was detected at the highest concentration of rAd-p21$^{WAF1/Cip1}$ treatment ($3.0\times10^9$ PN/ml) when compared to untreated cells (60.0±6.3 ng/ml vs. 165.1±9.0 ng/ml of protein, respectively. The highest dose of rAd-Empty treatment showed 170.2±10.3 ng/ml of intracellular PIP, unchanged from uninfected cells. Our previous studies have shown that 100% of human dermal fibroblasts are positive for transgene expression in this assay system as evaluated by FACS analysis (data not shown). Apoptosis assays by Annexin V staining and FACS were performed to determine the viability of cells and the data demonstrated that cells were not apoptotic (data not shown). These data show that an extracellular-associated peptide is attenuated after rAd-p21$^{WAF1/Cip1}$ treatment.

rAd-p21WAF1/Cip1 Attenuates Granulation Tissue Following rAd-PDGF-B Stimulation in Vivo.

To determine the effect of rAd-p21$^{WAF1/Cip1}$ on granulation tissue in vivo, a rat PVA sponge model was used (Buckley, A., et al., *Proc Natl Acad Sci USA,* 82(21):7340-4 (1985)). PVA sponges in rats were injected with $1\times10^9$ PN/sponge of rAd-PDGF-B as a stimulator of granulation tissue (Liechty, K. W., et al., *J Invest Dermatol,* 113(3):375-83 (1999)) and three days later rAd-p21$^{WAF1/Cip1}$ was administered at $5.0\times10^{10}$ PN/sponge (FIG. 2). rAd-Empty virus was also delivered to sponges at the same dose levels as rAd-PDGF-B and rAd-p21$^{WAF1/Cip1}$ to control for general effects that recombinant adenovirus may contribute to this model system. There was reduced granulation tissue both in quantity and cell density in rAd-PDGF-B/rAd-p21$^{WAF1/Cip1}$ treated sponges as assessed by Trichrome stain within PVA sponges at day 5 post the rAd-p21$^{WAF1/Cip1}$ delivery (FIG. 3). The vehicle/vehicle (FIG. 3) and rAd-Empty/rAd-Empty groups (not shown) had similar granulation tissue morphology as rAd-PDGF-B/rAd-p21$^{WAF1/Cip1}$ treatment groups (FIG. 3). Consistent with published reports, the highest granulation tissue fill was observed in rAd-PDGF-B/vehicle treatment group (77%; FIG. 3), demonstrating that the stimulator, PDGF-B enhanced growth response in this model (Liechty, K. W., et al., *J Invest Dermatol,* 113(3):375-83 (1999)). We observed 53% granulation tissue fill in rAd-PDGF-B/rAd-Empty, 28% in rAd-PDGF-B/rAd-p21$^{WAF1/Cip1}$, 24% in vehicle/vehicle, and 18% in rAd-Empty/rAd-Empty treatment groups (FIG. 3). Compared to rAd-PDGF-B/vehicle and rAd-PDGF-B/rAd-Empty treatment, rAd-PDGF-B followed by rAd-p21$^{WAF1/Cip1}$ treatment induced a 2.7- and 1.9-fold attenuation in granulation tissue fill, respectively (p<0.001 and p=0.05). In contrast, no significant differences were observed between vehicle/vehicle, rAd-Empty/rAd-Empty, and rAd-PDGF-B/rAdp21$^{WAF1/Cip1}$ treatment groups (p>0.3). Vehicle/vehicle, rAd-PDGF-B/vehicle, and rAd-PDGF-B/rAd-empty treatment groups were all significantly different from each other (p<0.001 and p=0.01, respectively). In a separate study, a dose response with rAd-p21$^{WAF1/Cip1}$ was performed between $1\times10^9$ and $5\times10^{10}$ PN/ml (Table 1). There was a 23% drop in granulation content when compared to maximum fill in rAd-PDGF-B/vehicle treatment at $1\times10^9$, 37% decrease at $1.0\times10^{10}$ and 47% reduction at $5\times10^{10}$ PN/ml. These data demonstrate a quantitative and qualitative reduction in granulation tissue after rAd-p21$^{WAF1/Cip1}$ treatment.

TABLE 1

Dose response percent decrease of granulation tissue fill within PVA sponges after rAd-p21$^{WAF1/Cip1}$ treatment.

| | Treatment Groups | | | |
|---|---|---|---|---|
| 1st injection | rAd-PDGF-B | rAd-PDGF-B | rAd-PDGF-B | rAd-PDGF-B |
| 2nd injection | vPBS | rAd-p21$^{WAF1/Cip1}$ ($1\times10^9$) | rAd-p21$^{WAF1/Cip1}$ ($1\times10^{10}$) | rAd-p21$^{WAF1/Cip1}$ ($5\times10^{10}$) |
| Granulation area$^a$ (percent fill) | 100% | 77% | 63% | 54% |

Figure 2:
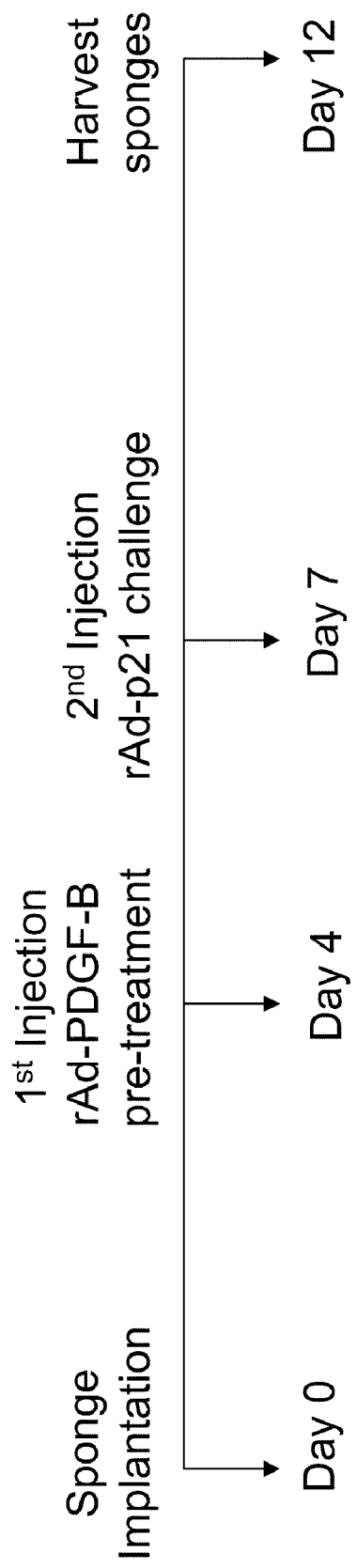
FIG. 2 illustrates an injection schedule in the rat PVA sponge model. PVA sponges were implanted on day 0 and rAd-PDGF-B pre-treatment was delivered 4 days post sponge implantation. rAd-p21$^{WAF1/Cip1}$ was delivered 3 days after rAd-PDGF-B pre-treatment and all sponges were harvested 5 days later.

Trichrome stained PVA sponge sections were analyzed by computer assisted image analysis for granulation fill area within sponges. Percent fill was calculated as area of granulation tissue/total area analyzed × 100. Refer to FIG. 2 for injection schedule timing. All rAd-PDGF treatments were dosed at 1 × 109 PN/sponge. Each treatment group represents the mean of 6 individual sponges and a minimum of 22 measurements per group. Data is representative of two separate experiments.
$^a$Normalized to % of maximum fill treatment (77%, rAd-PDGF-B/vPBS treatment).

Expression of p21$^{WAF-1/Cip-1}$ Protein In Vivo.

To validate transduction in vivo and link p21$^{WAF-1/Cip-1}$ expression with reduction of granulation tissue, we used an anti human p21$^{WAF-1/Cip-1}$ specific antibody to identify p21$^{WAF-1/Cip-1}$ expressing cells in the rat PVA sponge model. Five days after treatment with rAd-p21$^{WAF1/Cip1}$, p21$^{WAF-1/Cip-1}$ protein was localized within granulation tissue cells, which morphologically resembled inflammatory cells (FIG. 5C, small arrowhead) and fibroblasts-like cells. We did not observe p21$^{WAF-1/Cip-1}$ positive stained cells in either the vehicle/vehicle or rAd-PDGF-B/vehicle treatment groups.

While the predominant population of p21$^{WAF-1/Cip-1}$ expressing cells exhibited intense staining 5 days after rAd-p21$^{WAF1/Cip1}$ administration, we have currently not defined the peak response and duration of p21$^{WAF-1/Cip-1}$ protein expression in this model. However, rAd-p21$^{WAF1/Cip1}$ expression by RT-PCR peaked within one week and persisted beyond 30 days in a rabbit model of glaucoma filtration surgery (Perkins, T. W., et al., *Arch Ophthalmol*, 120(7):941-9 (2002)). These data support a link between reduction in granulation tissue and p21$^{WAF-1/Cip-1}$ expression in vivo.

Proliferation Index is Attenuated After rAd-p21$^{WAF1/Cip1}$ Treatment In Vivo.

To determine the proliferation status of granulation tissue after rAd-p21$^{WAF1/Cip1}$ delivery, BrdU and Ki67 immunohistochemical staining was performed on PVA sponge tissue. The percent of BrdU and Ki67 positive cells in vehicle/vehicle, rAd-PDGF-B/vehicle, rAd-PDGF-B/rAd-Empty, and rAd-PDGF-B/rAd-p21$^{WAF1/Cip1}$ treatment groups are presented in FIG. 4. The highest BrdU staining was observed in rAd-PDGF-B/vehicle and rAd-PDGF-B/rAd-Empty treatment groups (25% and 24%, respectively), demonstrating that rAd-PDGF-B promoted tissue proliferation and also suggesting that rAd-Empty treatment had minimal impact on proliferative status in vivo. The lowest percent BrdU stained cells was identified in rAd-PDGF-B/rAd-p21$^{WAF1/Cip-1}$ treatment group (9%). BrdU incorporation in the rAd-PDGF-B/rAd-p21$^{WAF1/Cip1}$ treatment group was significantly lower when compared to rAd-PDGF-B/vehicle and rAd-PDGF-B/rAd-Empty (p<0.01 for both comparisons). In addition, the vehicle/vehicle treatment group had 2-fold greater number of BrdU positive cells when compared to rAd-PDGF-B/rAd-p21$^{WAF1/Cip1}$ treatment group (18% vs. 9%, respectively).

Figure 4B:
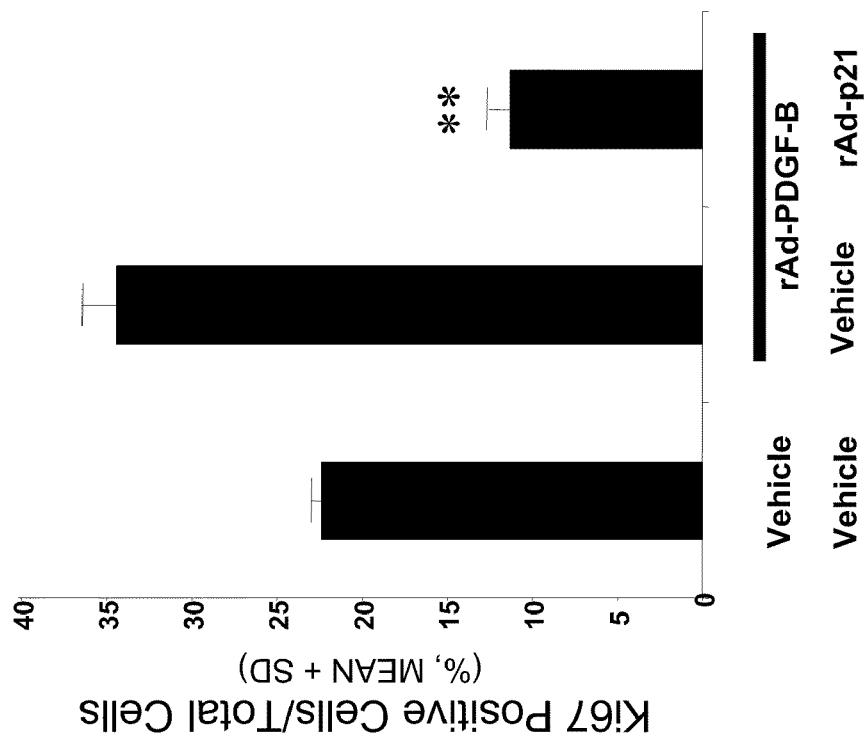
FIGS. 4A and 4B illustrate the proliferative index after rAd-p21$^{WAF1/Cip1}$ treatment in vivo. Mean percent of BrdU and Ki67 positive cells. Immunohistochemistry was performed with anti-BrdU and Ki67 antibodies in vehicle/vehicle, rAd-PDGF-B/vehicle, rAd-PDGF-B/rAd-Empty, and rAd-PDGF-B/rAd-p21$^{WAF1/Cip1}$ treated sponges. Comparisons are significant between rAd-PDGF-B/rAd-p21$^{WAF1/Cip1}$ treatment group vs. rAd-PDGF-B/vehicle and rAd-PDGF-B/rAd-Empty groups (*p<0.01) as well as rAd-PDGF-B/rAd-p21$^{WAF1/Cip1}$ treatment group vs. rAd-PDGF-B/vehicle and vehicle/vehicle treatment groups (**p<0.001). For BrdU, 9 fields from 3 sponges per treatment were counted. For Ki67, 4 sponges per treatment group were counted.
Figure 4A:
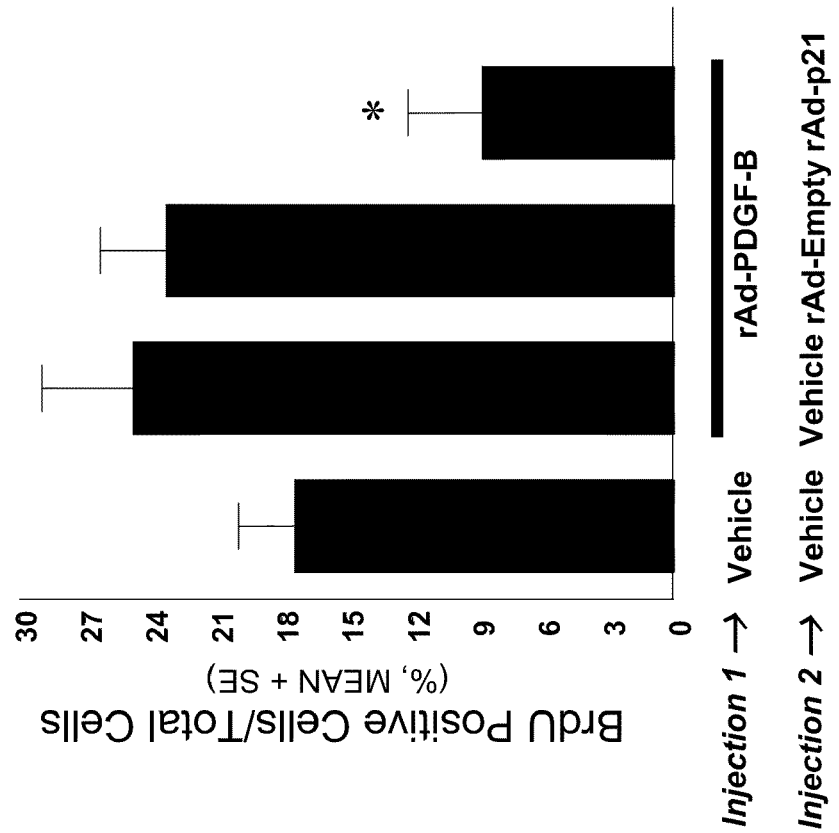

While BrdU incorporation requires S phase initiation, Ki67 or Mib1 antigen is expressed in all cell cycle phases except G$_0$ (Barnard, N. J., et al., *J Pathol*, 152(4):287-95 (1987). The analysis of Ki67 staining showed similar percentage of positive cells as BrdU staining (FIG. 4B). Proliferation indices of vehicle/vehicle and rAd-PDGF-B/vehicle treatment groups were 22% and 34%, respectively. In contrast, rAd-PDGF-B/rAd-p21$^{WAF1/Cip1}$ treatment groups revealed significantly less percent proliferating cells (11%) when compared to rAd-PDGF-B/vehicle and vehicle/vehicle treatment groups (p<0.001 for all comparisons). These data demonstrate that rAd-p21$^{WAF1/Cip-1}$ treatment attenuates granulation tissue in vivo by reducing cell proliferation.

SUMMARY

The etiologies of hypertrophic scars and keloids are unknown but likely arise from dysregulation in the normal wound healing response. Normal wound healing proceeds as a fibroproliferative response that develops into a fibrotic scar. Importantly, even in the best circumstances, the injury site is "patched" rather than "restored", and both form and function are affected by the mechanisms responsible for replacement verses tissue regeneration. The normal wound healing cascade is comprised of 3 temporal, overlapping responses including inflammation, proliferation and remodeling phases. In all phases, there exists an equilibrium between catabolic and metabolic processes involving growth-promoting factors and factors responsible for down-regulating the proliferative response. While significant progress has been made to elucidate the factors involved in stimulating a wound to heal, far less has been made with regard to the molecular processes, including cell cycle regulation and programmed cell death involved in normal wound healing responses. The data presented herein, underscores the important role that cell cycle regulation has on the processes involved in wound repair and scar formation.

Our studies demonstrate that the cell cycle of human primary dermal fibroblasts can be efficiently inhibited in human primary dermal fibroblasts with p21$^{WAF-1/Cip-1}$ delivered via a recombinant adenovirus. We showed a dose dependent increase in p21$^{WAF-1/Cip-1}$ protein expression that correlates with a dose dependent decrease in proliferative status as evidenced by BrdU staining in vitro. There were detectable anti-proliferative effects observed with control adenovirus treatment at the highest dose, but propidium iodide staining revealed that these cells had accumulated in G2/M, rather than G1, as in the case of the cells treated with rAd-p21$^{WAF-1/CIP-1}$ (data not shown). The observation that transduction with a high dose of recombinant adenovirus vector alone causes attenuation of cellular proliferation has been previously described and several studies report anti-tumor effects with high doses of recombinant adenovirus containing reporter genes (Erhardt, J. A. and R. N. Pittman, *Oncogene*, 16(4):443-51 (1998); Pierce, G. F., et al., *J Exp Med.* 167(3): 974-87 (1988); Teramoto, S., et al., *Hum Gene Ther.* 6(8): 1045-53 (1995)). Increasing levels of cellular p21$^{WAF-1/Cip-1}$ protein correlate to a decrease in proliferative response in human dermal primary fibroblasts.

The excessive accumulation and disorganization of extracellular matrix, namely collagen, is a hallmark of keloids and hypertrophic scars (Rockwell, W. B., et al. *Plast Reconstr Surg*, 84(5):827-37 (1989)). The two chemotherapeutic agents, mitomycin C and doxorubicin, have been reported to inhibit the wound healing response with mechanisms of action including reduction of ECM and cytotoxicity (Saika, S., et al., *Ophthalmic Res.* 29(2):91-102 (1997)). Our studies show that elevated levels of p21$^{WAF-1/Cip-1}$ in dermal primary fibroblasts reduced PIP levels in vitro. Interestingly, PIP levels were attenuated but not ablated suggesting that basal levels of PIP production are being maintained in viable cell populations. In contrast, while both mitomycin C and doxorubicin decreased PIP secretion, a dose dependent reduction in cell viability was observed and is likely causative of wound dehiscence observed in a wound healing animal model (Saika, S., et al., *Ophthalmic Res.* 29(2):91-102 (1997)). Further, PIP levels were not affected by rAd-Empty treatment suggesting that PIP attenuation was p21$^{WAF-1/Cip-1}$ specific. Transduced cells were transcriptionally active (data not shown) demonstrating that reduction in PIP is not a result of general transcriptional depression within the cell. We hypothesized that reduction of extracellular matrix production as a result of exogenously expressed p21$^{WAF-1/Cip-1}$ would have attenuating effects on granulation tissue production in vivo.

An animal model which exactly simulates the biochemical and pathophysiological parameters of human keloids and hypertrophic scars does not exist. In this report, we used an animal model system to address the effects of elevated p21$^{WAF-1/Cip-1}$ on granulation tissue in vivo. Granulation tissue is composed of fibroblasts, new capillaries, inflammatory cells and extracellular matrix and is a necessary and required element of wound repair. Disruption of the normal temporal and spatial formation of granulation tissue is implicated as a causative effect in hypertrophic scars and keloids. PDGF-BB is a potent stimulator of granulation tissue formation and recent reports have demonstrated potent pro-wound healing effects in wound impaired models (Liechty, K. W., et al., *J Invest Dermatol.* 113(3):375-83 (1999); Pierce, G. F., et al., *J Exp Med.* 167(3):974-87 (1988); Pierce, G. F., et al., *J Cell Biochem.* 45(4):319-26 (1991); Doukas, J., et al., *Hum Gene Ther.* 12(7):783-98 (2001)). Interestingly, addition of PDGF-BB to a scarless fetal model results in wound fibrosis and elevated levels of PDGF-BB have been associated with liver cirrhosis (Haynes, J. H., et al., *J Pediatr Surg.* 29(11):1405-8 (1994); Peterson, T. C. and R. A. Isbrucker, *Hepatology* 15(2):191-7 (1992)). We used rAd-PDGF-B to enhance cellular influx, proliferation and granulation tissue deposition and then followed with rAd-p21$^{WAF1/Cip1}$ treatment in the rat PVA sponge model to determine if p21$^{WAF-1/Cip-1}$ could attenuate these stimulatory effects in vivo.

Our results show that rAd-p21$^{WAF1/Cip-1}$ attenuated granulation fill both qualitatively and quantitatively when compared to rAd-PDGF-B treatment alone. The diminution of granulation fill after rAd-Empty treatment is consistent with our in vitro results and pales in effect when compared to rAd-p21$^{WAF1/Cip1}$ treatment. Initially, we hypothesized that rAd-Empty treatment alone may interfere with granulation tissue outcome via the well-documented immunomodulatory effects of the rAd delivery vehicle on the host (Nielsen, L. L., *Oncol Rep* 7(1):151-5 (2000); Kajiwara, K., et al., *Hum Gene Ther.*, 8(3):253-65 (1997); St George, J. A., et al., *Gene Ther,* 3(2):103-16 (1996); Brody, S. L., et al., *Hum Gene Ther,* 5(7): p. 821-36 (1994)). We repeatedly observed that the stimulatory and inhibitory effects of PDGF-BB and p21WAF-1/Cip-1 respectively, modulate granulation tissue activity over and above recombinant adenovirus derived responses. Critical to this observation is our demonstration of a rAd-p21$^{WAF1/Cip1}$ dose dependent attenuation of granulation tissue in vivo, further supporting gene specific activity in this model system.

We were able to demonstrate human p21$^{WAF-1/Cip-1}$ protein expression in sponges treated with rAd-p21$^{WAF1/Cip1}$, thus linking human p21$^{WAF-1/Cip-1}$ with reduction of granulation tissue. We also showed reduced proliferation by two separate assays in p21$^{WAF-1/Cip-1}$ treated sponges, supporting the direct anti-proliferative effects of p21$^{WAF-1/Cip-1}$ in vivo. Cell-specific protein expression was not determined in these studies but morphologically, our results suggest that both macrophages and fibroblasts can express exogenous p21$^{WAF-1/Cip-1}$ protein.

Skin, the largest organ of the body, offers local-regional delivery with limited systemic exposure, is accessible and can be non-invasively examined. Both viral and non-viral approaches have demonstrated gene transfer (Khavari, P. A., et al, *J Intern Med,* 252(1):1-10 (2002)). We present evidence here that the exogenously expressed cell cycle regulator, p21$^{WAF-1/Cip-1}$, delivered via a recombinant adenovirus attenuates proliferative responses associated with excessive scarring. With appropriate design and application schedule, p21$^{WAF-1/Cip-1}$ has therapeutic application in disorders of the skin such as keloids and hypertrophic scars where the pathophysiology stems from dysregulation of proliferative response.

Example 2

This example illustrates rAd-p21 delivery and p21$^{WAF-1/Cip-1}$ expression in wounds.

rAd-p21 gene delivery and expression over time was characterized in the rabbit ear excessive scar model after a single intradermal injection as follows:

Methods:

Two to four, 6-mm diameter wounds were induced per rabbit ear. Sample size for analysis consisted of three to eight wounds per treatment group. Two wounds from identical wounding positions on both ears were pooled and placed in a single tube to meet the tissue requirements for RT-PCR and PCR assays. This tube represented the average of two wounds and one assay sample. For PCR and RT-PCR assays at harvest time points 8 hours, days 1, 3, 5, 7 and 10, N=1 or 4 representing 2 or 8 wounds total. For day 14, one wound was placed in a single tube as one sample, therefore N=1 or 4 representing 1 or 4 wounds total per group. For morphological evaluation, one wound represented one sample and two to four samples were evaluated per group.

A vPBS treatment group served as vehicle control for both PCR/RT-PCR assays and morphological evaluation. rAd-Empty treatment served as control for adenoviral effects in this study.

Test Reagent Preparation: rAd-p21 and rAd-Empty: Stock virus was diluted on day 0 of the study in vPBS diluent and maintained on ice. The diluted viruses were brought to room temperature a half hour prior to intradermal injection into animals.

Rabbit Preparation: Female, New Zealand White rabbits were anesthetized with an intramuscular injection of 70 mg/kg of Ketamine, 5 mg/kg of Xylazine, and 0.1 mg/kg of Butorphanol. A hair depilator (Nair™) was applied to ears to remove hair and ears were rinsed with warm tap water and the surgical area was scrubbed with Betadine and isopropanol. Animals were transferred from the pre-operating room to the operating room.

Surgical Procedures and Treatments: Under sterile conditions, two to four, 6 mm wounds were made with a Trephine on the ventral side of each ear to the depth of the cartilage. The cartilage and overlying skin were removed with a hemostat from each wound. Wound marginal areas were prepared with Mastisol® and the wounds were covered with OpSite® dressing to prevent drying. Dressings remained on the wounds for the duration of the study. $2 \times 10^6$ or $2 \times 10^{10}$ PN per wound of rAd-p21 were injected intradermally around wound marginal areas in a total volume of 100 µL per wound using a 28G ½ insulin injection syringe. Injection sites on wounds were in positions 3, 6, 9 and 12 o'clock and within 2-3 mm of the wound margin areas. Procedures were repeated on both ears for all rabbits in groups 1, 3 and 4. One ear was wounded per rabbit in the rAd-Empty treatment group at days 1, 3 and 10 time points. Animals were returned to cages and allowed food and water ad libitum.

Endpoint Analysis: At specified sacrifice time points, animals were euthanized with an overdose of Euthasol CIII 200 mg/kg, iv and the rabbit ears were amputated at the base. Full-thickness wounds were excised with a 10 mm tissue biopsy punch and placed in a microcentrifuge tube containing 250 µL of QIAGEN RNAlater™ (RNA stabilization reagent). All tissues were immersed in the RNA stabilization reagent and stored at 4° C. for PCR and RT-PCR analysis. On the day

| Group | Treatment (Intradermal Dose) | Endpoint Analysis | Time Points for Analysis |
|---|---|---|---|
| 1 | vPBS | PCR, RT-PCR, Morphology | 8 hours; Days 1, 3, 5, 7, 10 and 14 |
| 2 | rAd-Empty ($2 \times 10^{10}$ PN/wound) | Morphology | Days 1, 3 and 10 |
| 3 | rAd-p21 ($2 \times 10^6$ PN/wound) | PCR, RT-PCR Morphology | 8 hours; Days 1, 3, 5, 7, 10 and 14 |
| 4 | rAd-p21 ($2 \times 10^{10}$ PN/wound) | PCR, RT-PCR Morphology | 8 hours; Days 1, 3, 5, 7, 10 and 14 |

14 time point, all procedures were the same as above except one wound from an identical ear wound position was placed in a microcentrifuge tube, representing one sample. For morphological evaluation, wounds were bisected, and half of the wound was frozen in Optimum Cryosection Temperature Compound (OCT) and the remaining half was fixed in 4% paraformaldehyde at 4° C. for 4 hours, transferred to 70% EtOH, and processed for Trichrome staining Morphological examination was performed on wound tissue sections for inflammation and wound healing responses.

Quantitative PCR/Quantitative RT-PCR and Preparation of Standard Curve: Quantitative PCR and RT-PCR (QPCR and QRT-PCR) procedures were used to quantify rAd-p21 DNA and transgene expression as previously described by Wen et al., *Exp Eye Res.* 77(3):355-65 (2003). DNA and RNA were co-extracted from approximately 50-100 mg of tissue using Tri-Reagent®.

Results:

rAd-p21 delivery and human $p21^{WAF-1/Cip-1}$ gene expression was characterized over time in the rabbit ear excessive scar model after a single intradermal dose was delivered immediately after wounding. QPCR and QRT-PCR techniques were implemented to quantify rAd-p21 DNA and human $p21^{WAF-1/Cip-1}$ gene expression in the wound area.

QPCR and QRT-PCR Evaluation: $2\times10^6$ or $2\times10^{10}$ PN per wound of rAd-p21 was delivered by a single intradermal injection to rabbit ear wounds. Each rAd-p21 analyzed sample was $2\times10^6$ or $2\times10^{10}$ PN per each of two wounds combined thus totaling $4\times10^6$ or $4\times10^{10}$ total PN, respectively. On day 14, there was only one wound per sample.

The highest rAd-p21 DNA levels were observed at 8 hours and one day from both the low and the high rAd-p21 dose groups. DNA levels decreased over a 14 day period by over 1.0 and 3.0 logs in the low and the high dose rAd-p21 groups, respectively. The highest rAd-p21 RNA level was observed at day 3 post intradermal injection in the high dose group. RNA levels dropped approximately 0.5-1.0 log by days 7, 10 and 14 as compared to peak levels at day 3. The RNA levels in the low dose rAd-p21 group were undetectable (Below Quantifiable levels; BQL) 8 hours and one day after treatment. The onset of detectable RNA expression in the low dose rAd-p21 group was observed on day 3. Peak RNA levels were observed on days 3 and 14 with no significant difference between day 3 and day 14 in the low dose group (p<0.5; Fisher's Post Hoc ANOVA). There were approximately 0.5-1.0 log lower RNA levels at days 5, 7 and 10 when compared to the RNA levels on days 3 and 14 in the low dose rAd-p21 group. As expected, all vPBS samples were negative confirming no cross contamination of samples or cross reactivity of human p21 primer sequence with endogenous rabbit sequence. This RNA expression profile at the low dose over time demonstrates a similar expression trend as the high dose rAd-p21 group.

Morphological Evaluation: The morphological changes in rabbit wounds followed typical phases of acute wound healing processes. Briefly, at 8 hours post-wounding, inflammatory cell infiltration in wounds was observed. Inflammatory cell influx increased in all wounds on days 1 and 3. By day 5, granulation tissue started to fill the wound beds and epithelial migrating tongues were observed around the wound edges. At days 7, 10 and 14, wound beds were filled with granulation tissue and covered by epithelium. Thinner granulation tissue and epithelial layers were noticed in the low rAd-p21 dose treatment group when compared to the remaining groups at days 10 and 14. However, the low dose rAd-p21 group showed denser cellularity than the high dose group at day 14. This data suggests that rAd-p21 can attenuate the volume of granulation tissue and the thickness of epithelium in the wound scar.

Discussion:

Human rAd-p21 DNA delivery and $p21^{WAF-1/Cip-1}$ RNA expression were detected in both high and low doses of rAd-p21 treatment groups in the rabbit ear wounds. $p21^{WAF-1/Cip-1}$ RNA levels were maintained over a 14 day period in both the high and low dose groups.

Example 3

This example illustrates that rAd-p21 treatment inhibits scar thickness.

An excessive scar rabbit model was used to determine the effect of rAd-p21 treatment on scar thickness. Enhanced scarring was induced by injections of PDGF-BB (2 μg) protein into a rabbit ear wound as described previously. A second injection of $2\times10^{10}$ PN of either rAd-p21 or rAd-Empty followed seven days later. Scar height was measured as a response to treatment and effects were maximally observed at approximately 11 days post rAd-p21 treatment. Scar tissue was measured between day 18 and 35 (post initial wounding) and tissue was harvested on day 35 after the initial PDGF-BB injection.

FIG. 5 demonstrates that rAd-p21 treatment attenuates scar thickness after intradermal delivery in the rabbit ear excessive scar model. This data supports previous observations that in the normal scar environment low doses of rAd-p21, for example, $2\times10^6$ PN per wound ($7\times10^6$ PN/cm$^2$) are efficacious in reducing scar height in this model. When PDGF-BB is used to induce enhanced scar formation, more rAd-p21 is required to overcome these scar effects.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method for reducing scarring, the method comprising administering a replication deficient adenoviral vector comprising an expression cassette to skin of a subject having a wound, wherein the expression cassette comprises a cytomegalovirus immediate early (CMV) promoter operably linked to a polynucleotide encoding $p21^{WAF1/Cip1}$, resulting in wound closure and reduced scarring.

2. The method of claim 1, wherein the administrating results in decreased keloids or hypertophic scarring at the wound compared to scarring on an untreated wound.

3. The method of claim 1, wherein the adenoviral vector is administered at a dose of between $10^5$ and $10^9$ particle number (PN) per cm$^2$ of the wound.

4. The method of claim 1, wherein the vector is administered in a biocompatible matrix.

5. The method of claim 4, wherein the matrix comprises collagenous, metal, hydroxyapatite, bioglass, aluminate, bioceramic materials, purified proteins or extracellular matrix compositions.

6. The method of claim 4, wherein the matrix is a collagen matrix.

7. The method of claim 1, wherein the skin is burned.

8. The method of claim 1, wherein the vector comprises a partial or total deletion of protein IX.

\* \* \* \* \*